United States Patent
Oh et al.

(10) Patent No.: US 10,676,701 B2
(45) Date of Patent: Jun. 9, 2020

(54) CONSUMER PRODUCT COMPOSITIONS COMPRISING MICROCAPSULES

(71) Applicant: The Procter & Gamble Company, Cincinnati, OH (US)

(72) Inventors: Hiroshi Oh, Cincinnati, OH (US); Dorothy A Hall, Blanchester, OH (US); Pierre Verstraete, Woluwe St Lambert (BE); Olivier Fasbender, Ixelles (BE); Johan Smets, Lubbeek (BE); Steven Daryl Smith, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/919,281

(22) Filed: Mar. 13, 2018

(65) Prior Publication Data

US 2018/0265827 A1    Sep. 20, 2018

Related U.S. Application Data

(60) Provisional application No. 62/472,012, filed on Mar. 16, 2017.

(51) Int. Cl.

| | | |
|---|---|---|
| *C11D 3/50* | (2006.01) | |
| *A61L 9/04* | (2006.01) | |
| *A61K 8/00* | (2006.01) | |
| *C11D 17/00* | (2006.01) | |
| *C11D 3/22* | (2006.01) | |
| *A61K 8/73* | (2006.01) | |
| *A61K 8/11* | (2006.01) | |
| *A61K 8/81* | (2006.01) | |
| *A61Q 5/12* | (2006.01) | |
| *A61Q 13/00* | (2006.01) | |
| *C11D 11/00* | (2006.01) | |
| *C11D 3/37* | (2006.01) | |

(52) U.S. Cl.
CPC ............ *C11D 17/0039* (2013.01); *A61K 8/11* (2013.01); *A61K 8/736* (2013.01); *A61K 8/8152* (2013.01); *A61Q 5/12* (2013.01); *A61Q 13/00* (2013.01); *C11D 3/227* (2013.01); *C11D 3/505* (2013.01); *C11D 11/0017* (2013.01); *A61K 2800/412* (2013.01); *C11D 3/3757* (2013.01)

(58) Field of Classification Search
CPC ... C11D 17/0039; C11D 3/505; C11D 3/3757; C11D 3/227
USPC ........................................................ 512/4, 1
See application file for complete search history.

(56) References Cited

U.S. PATENT DOCUMENTS

| | | | |
|---|---|---|---|
| 2,396,278 A | 3/1946 | Lind | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Kosmin | |
| 3,929,678 A | 12/1975 | Laughlin et al. | |
| 6,855,680 B2 | 2/2005 | Smerznak et al. | |
| 7,208,459 B2 | 4/2007 | Sadlowski et al. | |
| 7,294,611 B2 | 11/2007 | Metrot et al. | |
| 7,686,892 B2 | 3/2010 | Smets et al. | |
| 8,268,016 B2 | 9/2012 | Batchelor et al. | |
| 9,162,085 B2 * | 10/2015 | Dihora | A61K 8/11 |
| 9,186,642 B2 | 11/2015 | Dihora et al. | |
| 9,221,028 B2 | 12/2015 | Dihora et al. | |
| 2003/0180369 A1 * | 9/2003 | Grisoni | A61K 8/11 424/490 |
| 2003/0224959 A1 | 12/2003 | Smith | |
| 2005/0281886 A1 | 12/2005 | Cattaneo | |
| 2011/0268778 A1 | 11/2011 | Dihora et al. | |
| 2011/0268802 A1 | 11/2011 | Dihora et al. | |
| 2011/0269657 A1 | 11/2011 | Dihora et al. | |
| 2012/0282309 A1 | 11/2012 | Dihora | |
| 2017/0002302 A1 | 1/2017 | Dihora | |
| 2018/0264425 A1 | 9/2018 | Verstraete | |

FOREIGN PATENT DOCUMENTS

| | | |
|---|---|---|
| WO | WO2008005693 A2 | 1/2008 |
| WO | WO2012138696 A2 | 10/2012 |
| WO | WO2017004340 A1 | 1/2017 |

OTHER PUBLICATIONS

International Search Report and Written Opinion dated Jun. 27, 2018, 12 pgs.
International Search Report dated May 7, 2018, 14 pgs.
U.S. Appl. No. 15/919,273, filed Mar. 13, 2018, Pierre Verstraete et al.

* cited by examiner

*Primary Examiner* — Jessica Whiteley
(74) *Attorney, Agent, or Firm* — Gregory S. Darley-Emerson

(57) ABSTRACT

A consumer product composition comprises a consumer product adjunct ingredient, a microcapsule, and deposition polymer disposed on an outer surface of the microcapsule. The deposition polymer has a Water Uptake Value (WUV) of at least about 2 grams per gram, as determined according to the WATER UPTAKE VALUE TEST METHOD. The microcapsule comprises a shell material encapsulating a core material, wherein the shell material comprises a polyacrylate and the core material comprises a benefit agent.

38 Claims, 3 Drawing Sheets

CONSUMER PRODUCT COMPOSITIONS COMPRISING MICROCAPSULES

FIELD OF THE INVENTION

The present invention relates to consumer product compositions comprising microcapsules comprising deposition polymer disposed thereon, and methods of depositing microcapsules.

BACKGROUND OF THE INVENTION

Consumers often desire consumer products for the many benefits they may provide. For example, it is not uncommon for a particular consumer to have in their home laundry detergents, fabric softeners, shampoos, conditioners, body washes, deodorants, fine fragrances, shaving gels, and the like. Often, such consumer products also include benefit agents such as perfumes. Benefit agents such as perfumes may delight the user by providing a freshness feeling and may serve as a signal to the user that the product may still be working or that the product is still present. Yet because of the volatility of many perfumes, a consumer may be unable to notice the perfume shortly after using the consumer product, potentially leading the user to believe the benefits are dissipating or have dissipated. Consequentially, it may be desirable to have technologies that improve the noticeability of perfumes in consumer products, especially after use of the consumer products.

Microcapsules have been used previously to encapsulate benefit agents such as perfumes in consumer products in order to provide longer lasting freshness benefits after use of the consumer product. Microcapsules typically contain the perfume until the capsule is fractured during use, thereby releasing the perfume to provide freshness benefits.

It remains a challenge, however, to deposit microcapsules effectively on treated surfaces, especially if the microcapsules are contained in a consumer product composition that is diluted into a wash solution during use for treating surfaces such as fabric fibers (e.g. laundry detergents or fabric softeners), or in consumer product compositions used to treat surfaces such as human hair which are rinsed from the surface during use. It has thus been desired to improve the deposition of microcapsules on surfaces to enhance the delivery of benefit agents to provide longer lasting benefits during and after use of the consumer product.

SUMMARY OF THE INVENTION

The present invention relates to a consumer product composition comprising a consumer product adjunct ingredient and microcapsules having deposition polymer disposed on an outer surface of the microcapsules. The deposition polymer has a Water Uptake Value (WUV) of at least 2 grams per gram (g/g), as determined according to the WATER UPTAKE VALUE ("WUV") TEST METHOD described herein. The deposition polymer is preferably chitosan. Preferred chitosans have a weight average molecular weight of at least about 100 kDa (kilodaltons) and/or a degree of de-acetylation of at least about 60%. The microcapsules comprise a shell material encapsulating a core material, with the core material being disposed within the shell material. The shell material comprises a polyacrylate polymer and the core material comprises a benefit agent, preferably a perfume.

The particular deposition polymers having a WUV of at least 2 g/g of the present invention can be effective in improving the deposition of polyacrylate microcapsules on treated surfaces, when the consumer product compositions are used.

The present invention further relates to a method of depositing microcapsules on a surface comprising the step of contacting the surface with a consumer product composition of the present invention.

DETAILED DESCRIPTION OF THE INVENTION

Figure 1A:
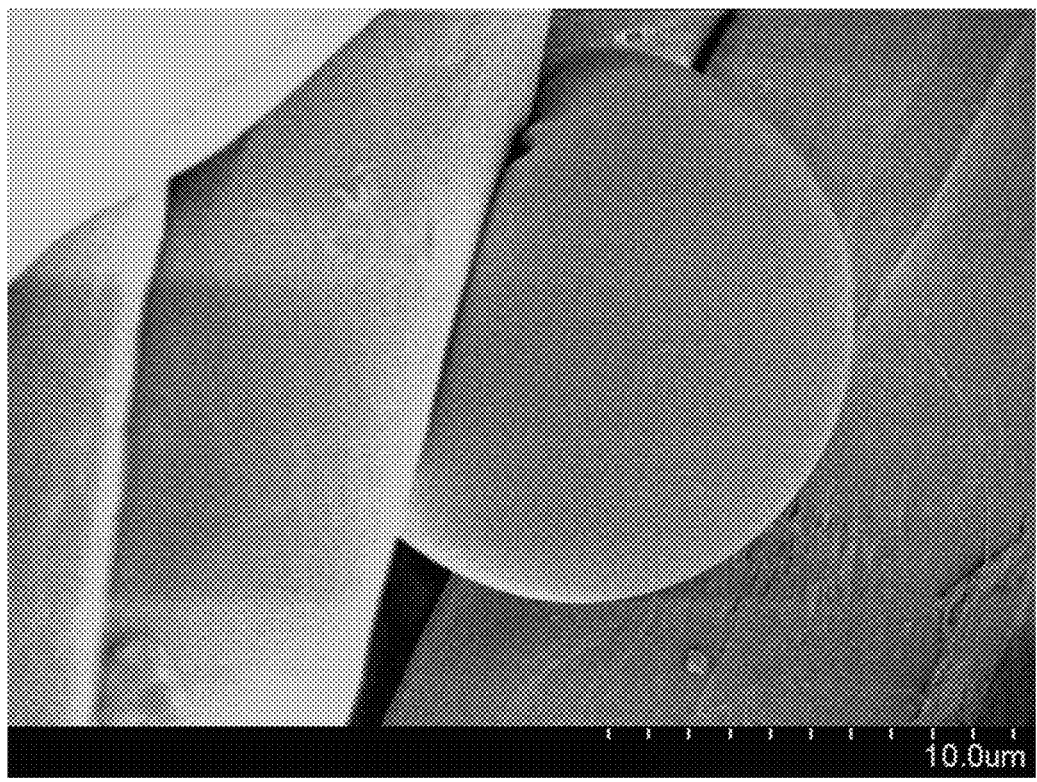
FIG. 1A is a micrograph showing a spherical microcapsule comprising a shell material comprising polyacrylate polymer, which has not been coated with deposition polymer, that has been deposited on a fabric after a typical fabric washing process.

The present invention relates to consumer product compositions comprising a consumer product adjunct ingredient, microcapsules, and deposition polymer having a WUV of at least 2 g/g disposed on the outer surface of the microcapsules.

Consumer Product Compositions

Consumer product compositions of the present invention include, but are not limited to, compositions for treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); shaving; body sprays; and fine fragrances like colognes and perfumes; compositions for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps, shampoos, lotions, oral care implements, and clothing; products such as wet or dry bath tissue, facial tissue, disposable handkerchiefs, disposable towels, and/or wipes; products relating to catamenial pads, incontinence pads, interlabial pads, panty liners, pessaries, sanitary napkins, tampons and tampon applicators, and/or wipes.

Preferred consumer product compositions herein include fabric softening compositions and hair conditioning compositions. Such compositions typically comprise a consumer product adjunct ingredient comprising cationic surfactant and/or silicone. Such consumer product adjunct ingredients typically serve as conditioning agents in the compositions.

Deposition Polymer

The present invention utilizes a deposition polymer having a WUV of at least 2 g/g which is disposed on the outer surface of the microcapsules in order to enhance the deposition of the microcapsules (e.g. onto fabrics or onto hair) during use of the consumer product composition.

The deposition polymer will have a WUV of at least 2 g/g, preferably at least about 3 g/g, and preferably at least about 4 g/g, as determined according to the WATER UPTAKE VALUE TEST METHOD described herein.

In this regard, the deposition polymer acts as a gelling polymer when disposed on the outer surface of the microcapsules. Polymers with higher Water Uptake Values tend to have higher gelling capacity. The gelling capacity of the polymer is responsible for the solid-like, viscoelastic properties of the polymer which tends to increase the viscosity and adhesiveness of the polymer. As such, it has been found that deposition polymers having a WUV of at least about 2 g/g enhance deposition of the microcapsules during use, while polymers having a WUV less than about 2 g/g tend not to enhance deposition of the microcapsules during use.

The deposition polymer is typically present in an amount of from about 0.01% to about 8%, preferably from about 0.05% to about 5%, preferably from about 0.1% to about 3%, preferably from about 0.5% to about 1.5%, by weight of the microcapsules.

The deposition polymer is preferably selected from the group consisting of chitosan, cationic co-polymer, nonionic terpolymer, block co-polymer, and combinations thereof.

Chitosan

The chitosan utilized as a deposition polymer in the present invention as a deposition polymer is a linear polysaccharide comprising randomly distributed β-(1,4)-linked D-glucosamine (deacetylated unit) and N-acetylglucosamine (acetylated unit) and generally has the following structure:

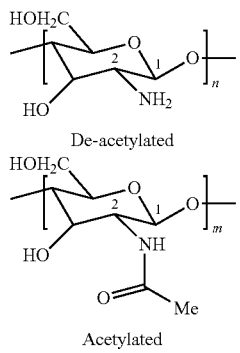

% DeAcetylation=$100n/(n+m)$ wherein n and m vary depending on the average molecular weight of the chitosan and the degree of deacetylation of the chitosan. The degree of deacetylation (% deacetylation) of the chitosan is equal to $100n/(n+m)$.

It is believed the effectiveness of the chitosan deposition polymer as a coating in improving the deposition of microcapsules onto the surface being treated with the consumer product of the present invention is based upon the degree of solubility of the chitosan material in pH buffer solution at a given pH. Preferred chitosans exhibit lower degree of solubility across the pH ranges of 2-10, preferably being soluble in pH buffer solution only at low pH, such as pH of 7 or less, preferably pH of 4 or less. The solubility of the chitosan is determined according to the SOLUBILITY TEST METHOD herein.

The solubility of chitosan in pH buffer solution is typically affected by the degree of deacetylation of the chitsoan and the weight average molecular weight of the chitosan. The degree of deacetylation of the chitosan can be determined according to the DEGREE OF DEACETYLATION TEST METHOD hereinbelow. The weight average molecular weight of the chitosan can be determined according to the MOLECULAR WEIGHT TEST METHOD hereinbelow.

The chitosan of the present invention has a weight average molecular weight of at least about 100 kDa (kilodaltons) and/or a degree of deacetylation of at least about 60%.

The chitosan of the present invention can have lower degree of deacetylation values, if the chitosan has relatively higher weight average molecular weight. The chitosan may also have lower weight average molecular weight values, if the chitosan has relatively higher degree of deacetylation values. Preferred chitosans have degree of deacetylation values and weight average molecular weight values that are both relatively high, which tend to exhibit lower solubility in pH buffer solution across the pH range of 2-10.

In one aspect, the chitosan of the present invention can have a degree of deacetylation of at least about 60% and a weight average molecular weight of at least about 10 kDa.

In one aspect, the chitosan of the present invention can have a weight average molecular weight of at least about 100 kDa and a degree of deacetylation of at least about 50%.

In one aspect, the chitosan of the present invention has either: (i) a weight average molecular weight of at least about 500 kDa and a degree of de-acetylation of at least about 50%, or (ii) a weight average molecular weight of at least 10 kDa and a degree of de-acetylation of at least about 70%.

In one aspect, the chitosan has a degree of deacetylation of at least about 60%, preferably at least about 70%, and preferably at least about 75%.

In one aspect, the chitosan has a weight average molecular weight of at least about 100 kDa, preferably at least about 200 kDa, and preferably at least about 400 kDa.

The amine group of chitosan has a $pK_a$ of about 6.5 and results in protonation of the chitosan in acidic to neutral solutions, with the charge density largely dependent upon the degree of deacetylation of the chitosan and the pH of solution. As such, chitosan of the present invention is typically cationic and can readily bind to anionically charged surfaces.

The chitosan is generally disposed on the outer surface of the polyacrylate microcapsules. The chitosan tends to adhere to the outer surface of microcapsules due to the anionically charged outer surface of the polyacrylate microcapsules through the protonated amino groups of the chitosan to form a gel. When used in a consumer product application, such as treating fabrics or hair in a typical wash/rinse solution and process, the gel tends to become more hydrophobic based on the increased pH of the wash/rinse solution due to deprotonation of the amino group. These hydrophobic gels tend to more effectively deposit and adhere to the treated surfaces, such as the treated fibers of a fabric or the treated hair of a consumer, thereby increasing the deposition of the chitosan-coated microcapsules versus microcapsules that are not coated with chitosan.

The chitosan is combined with the microcapsules, thereby becoming disposed on the outer surface of the microcapsules, before the microcapsules are combined with the consumer product adjunct ingredients to form the consumer product compositions of the present invention.

FIG. 1A is a micrograph showing a spherical microcapsule comprising a shell material comprising polyacrylate polymer, which has not been coated with deposition polymer, that has been deposited on a terry cotton fabric after a typical fabric washing process. Such deposition tends to occur through a filtration mechanism whereby the microcapsules become entrapped in the fibers of the fabric during agitation of the wash/rinse solution in the washing process. As can be seen in FIG. 1A, the microcapsule appears to be mechanically held in place via entrapment between the fibers of the fabric.

Figure 1B:
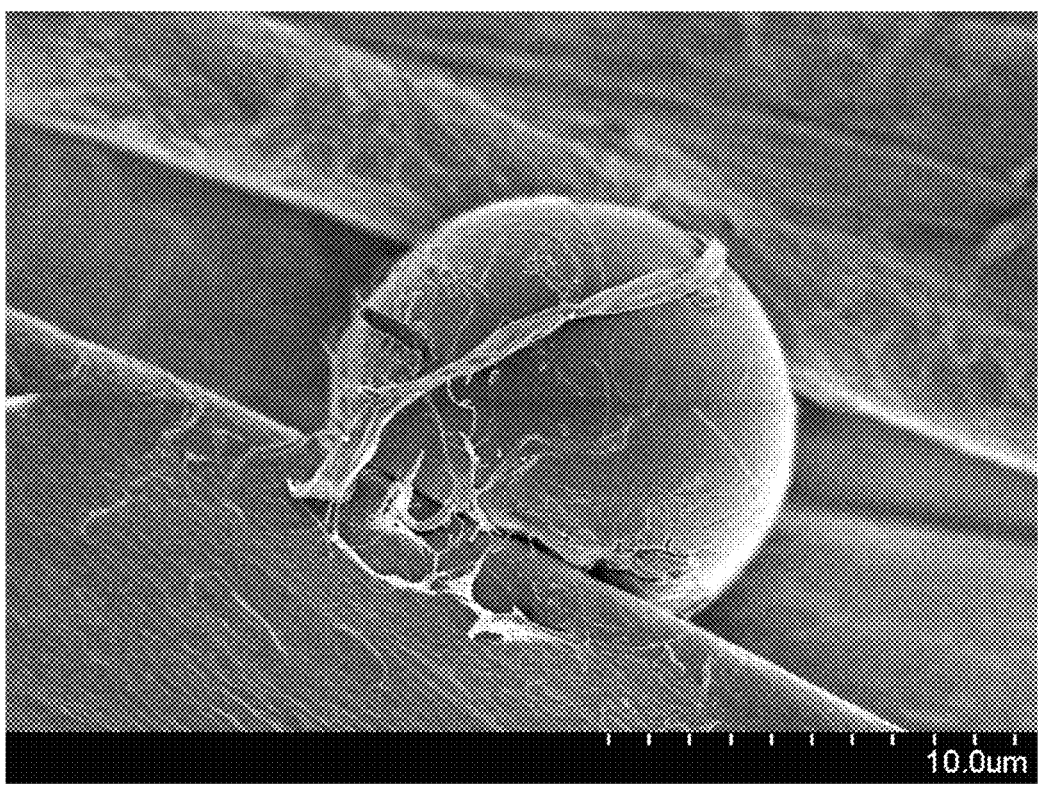
FIG. 1B is a micrograph showing a spherical microcapsule comprising a shell material comprising a polyacrylate polymer, which has been coated with chitosan deposition polymer of the present invention, that has been deposited on a fabric after a typical fabric washing process.

FIG. 1B is a micrograph showing a spherical microcapsule comprising a shell material comprising a polyacrylate polymer, which has been coated with chitosan deposition polymer of the present invention, that has been deposited on a fabric after a typical fabric washing process. As can be seen in FIG. 1B, the gelling chitosan deposition polymer coating on the microcapsule serves to adhere the microcapsule to the fiber of the fabric. As such, the microcapsule can be deposited on the fibers of the fabric by adherence due to the chitosan deposition polymer coating on the microcapsule in addition to the filtration mechanism whereby the microcapsule is entrapped between the fibers of the fabric as shown in FIG. 1A.

Chitosan is preferably incorporated in the present invention in an amount of from about 0.01% to about 8%, preferably from about 0.05% to about 5%, preferably from about 0.1% to about 3%, preferably from about 0.5% to about 1.5%, by weight of the microcapsules.

The chitosan deposition polymer of the present invention will have a Water Uptake Value, as measured by the WATER UPTAKE VALUE TEST METHOD herein, of at least about 2 grams/gram, preferably at least about 3 g/g, and preferably at least about 4 g/g.

The chitosan of the present invention preferably has a viscosity of at least about 0.01 poise, preferably from about 0.01 to about 25 poise, preferably from about 0.02 to about 24 poise, and preferably from about 0.02 to about 23 poise, as measured by the VISCOSITY TEST METHOD herein.

Cationic Co-Polymer

The cationic co-polymer utilized as a deposition polymer in the present invention is a random co-polymer comprising monomers selected from the group consisting of acrylamide ("AAM"), dimethyl acrylamide ("DMAA"), acrylamidopropyl trimethylamonium chloride ("APTAC"), methacrylamidopropyl trimethylammonium chloride ("MAPTAC"), and combinations thereof, wherein such cationic co-polymers have a formula:

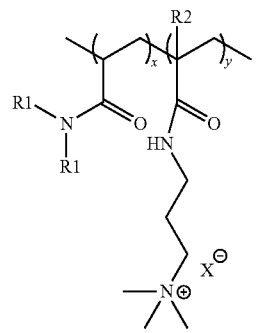

wherein x is an integer selected such that the monomer units constitute less than about 91% by weight of the cationic co-polymer, preferably from 0% to about 91% by weight of the cationic co-polymer, preferably from about 10% to about 85% by weight of the cationic co-polymer, preferably from about 15% to about 60% by weight of the cationic co-polymer, or preferably from about 15% to about 50% by weight of the cationic co-polymer;

y is an integer selected such that the monomer units constitute greater than about 9% by weight of the cationic co-polymer, preferably from about 9% to 100% by weight of the cationic co-polymer, preferably from about 15% to about 90% by weight of the cationic co-polymer, preferably from about 40% to about 85% by weight of the cationic co-polymer, or preferably from about 50% to about 85% by weight of the cationic co-polymer;

each R1 is independently selected from the group consisting of H and $CH_3$;

each R2 is independently selected from the group consisting of H and $CH_3$; and $X^-$ is a charge-balancing anion, preferably selected from the group consisting of chloride ion, bromide ion, and iodide ion.

It is believed the effectiveness of the cationic co-polymer as a coating in improving the deposition of microcapsules onto the surface being treated with the consumer product of the present invention is affected by the viscosity of the polymer (as measured according to the VISCOSITY TEST METHOD herein), which relates to the molecular weight of the cationic co-polymer. The effectiveness of the cationic co-polymer as a coating can also be affected by the Water Uptake Value of the cationic co-polymer (as measured by the WATER UPTAKE VALUE TEST METHOD herein), which relates to the gelling capacity of the cationic co-polymer.

The cationic co-polymer of the present invention has a viscosity of at least 0.09 poise, preferably from 0.09 to about 50 poise, preferably from 0.09 to about 25 poise, preferably from about 2 to about 20 poise, preferably from about 2 to about 15 poise, and preferably from about 5 to about 15 poise, as measured by the VISCOSITY TEST METHOD herein.

The number average molecular weight of the cationic co-polymer can be determined according to the MOLECULAR WEIGHT TEST METHOD hereinbelow. The cationic co-polymer of the present invention preferably has a number average molecular weight of from about 10 to about 5,000 kDa (kilodaltons), preferably from about 10 to about 2,500 kDa, preferably from about 20 to about 2,500 kDa, preferably from about 50 to about 2,500 kDa, preferably from about 20 to about 900 kDa, preferably from about 30 to about 500 kDa, and preferably from about 50 to about 300 kDa.

Surface charge of the cationic co-polymer of the present invention is typically cationic and can readily bind to anionically charged surfaces. The cationic co-polymer is generally disposed on the outer surface of the polyacrylate microcapsules due to a favored adhesion energy between two surfaces. The cationic co-polymer tends to adhere to the outer surface of microcapsules to form a deformable viscous gel layer. These hydrophobic gels tend to more effectively deposit and adhere to the treated surfaces, such as the treated fibers of a fabric or the treated hair of a consumer, thereby increasing the deposition of the cationic co-polymer-coated microcapsules versus microcapsules that are not coated with cationic co-polymer.

The cationic co-polymer is combined with the microcapsules, thereby becoming disposed on the outer surface of the microcapsules, before the microcapsules are combined with the consumer product adjunct ingredients to form the consumer product compositions of the present invention.

Cationic co-polymer is preferably incorporated in the present invention in an amount of from about 0.01% to about 8%, preferably from about 0.05% to about 5%, preferably from about 0.1% to about 3%, preferably from about 0.5% to about 1.5%, by weight of the microcapsules.

The cationic co-polymer of the present invention preferably has a Water Uptake Value, as measured by the WATER UPTAKE VALUE TEST METHOD herein, of at least about 2 grams/gram, preferably from about 5 to about 50 g/g, preferably from about 8 to about 40 g/g, preferably from about 10 to about 40 g/g, and preferably from about 15 to about 40 g/g.

A preferred cationic co-polymer has the formula above wherein x is an integer selected such that the monomer units constitute about 40% by weight of the cationic co-polymer and y is an integer selected such that the monomer units constitute about 60% by weight of the cationic co-polymer, R1 is H, and R2 is H. Such a preferred cationic co-polymer has a viscosity of about 10 poise, as measured by the VISCOSITY TEST METHOD herein, and a Water Uptake Value of about 32, as measured by the WATER UPTAKE VALUE TEST METHOD herein. Such a preferred cationic co-polymer is commercially available from Ashland Specialty Chemical Inc. under the trade name N-Hance™ SP-100.

The cationic co-polymer of the present invention is made according to the following general procedure. The desired monomers (AAM, DMAA, APTAC, and/or MAPTAC) are added to a reaction vessel with water. The reaction vessel is sparged with nitrogen to remove oxygen from the system and maintain a nitrogen atmosphere in the reaction vessel. The contents of the reaction vessel are heated to an elevated temperature (e.g. 60° C.) and an initiator solution is added. The contents of the reaction vessel are maintained at elevated temperature for several hours (e.g. 48 hours).

The viscosity and molecular weight of the resulting cationic co-polymer can be impacted by the level of initiator utilized in the reaction vessel. Such initiators can be added to the reaction vessel as 1% or 10% solutions in water, by weight. Suitable initiators include 2.2'-azobis(2-methylpropionamidine) dihydrochloride, available from Wako Chemicals under the trade name V-50.

Nonionic Terpolymer

The nonionic terpolymer utilized as a deposition polymer in the present invention is a random terpolymer comprising monomers selected from the group consisting of acrylamide ("AAM"), dimethyl acrylamide ("DMAA"), dimethylamino propyl-acrylamide ("DMAPA"), dimethylamino propylmethacrylamide ("DMAPMA"), N-alkyl acrylamide ("AAA"), N-octadecyl acrylamide ("ODAA"), and combinations thereof, wherein such nonionic terpolymers have a formula:

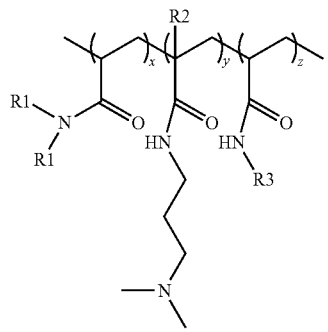

wherein x is an integer selected such that the monomer units constitute from about 65% to about 91% by weight of the nonionic terpolymer, preferably from 67% to about 90% by weight of the nonionic terpolymer, preferably from about 69% to about 89% by weight of the nonionic terpolymer, preferably from about 72% to about 87% by weight of the nonionic terpolymer, or preferably from about 75% to about 85% by weight of the nonionic terpolymer;

y is an integer selected such that the monomer units constitute from about 6% to about 35% by weight of the nonionic terpolymer, preferably from about 7% to about 30% by weight of the nonionic terpolymer, preferably from about 8% to about 25% by weight of the nonionic terpolymer, preferably from about 10% to about 20% by weight of the nonionic terpolymer, or preferably from about 12% to about 15% by weight of the nonionic terpolymer;

z is an integer selected such that the monomer units constitute from about 1% to about 4% by weight of the nonionic terpolymer, preferably from about 2% to about 3.5% by weight of the nonionic terpolymer, or preferably from about 2.5% to about 3% by weight of the nonionic terpolymer;

each R1 is independently selected from the group consisting of H and $CH_3$;

each R2 is independently selected from the group consisting of H and $CH_3$; and each R3 is independently a $C_{12}$-$C_{32}$ alkyl group, preferably a $C_{12}$-$C_{18}$ alkyl group, or preferably a $C_{18}$ alkyl group.

It is believed the effectiveness of the nonionic terpolymer as a coating in improving the deposition of microcapsules onto the surface being treated with the consumer product of the present invention is affected by the viscosity of the polymer (as measured according to the VISCOSITY TEST METHOD herein), which relates to the molecular weight of the nonionic terpolymer. The effectiveness of the nonionic terpolymer as a coating can also be affected by the Water Uptake Value of the nonionic terpolymer (as measured by the WATER UPTAKE VALUE TEST METHOD herein), which relates to the gelling capacity of the nonionic terpolymer. The effectiveness of the nonionic terpolymer as a coating can also be affected by the hydrophobicity of the nonionic terpolymer by incorporating an optimal amount of N-alkyl acrylamide monomer, especially N-octadecyl acrylamide.

The nonionic terpolymer of the present invention has a viscosity of at least 0.8 poise, preferably from 0.8 to about 50 poise, preferably from 0.8 to about 25 poise, preferably from about 3 to about 24 poise, or preferably from about 5 to about 23 poise, as measured by the VISCOSITY TEST METHOD herein.

The number average molecular weight of the nonionic terpolymer can be determined according to the MOLECULAR WEIGHT TEST METHOD hereinbelow. The nonionic terpolymer of the present invention preferably has a number average molecular weight of from about 100 to about 5,000 kDa (kilodaltons), preferably from about 100 to about 3,000 kDa, preferably from about 500 to about 2,500 kDa, preferably from about 1,000 to about 2,500 kDa, and preferably from about 2,000 to about 2,200 kDa.

Surface charge of the nonionic terpolymer of the present invention is typically nonionic. The nonionic terpolymer is generally disposed on the outer surface of the polyacrylate microcapsules due to a favored adhesion energy between two surfaces. The nonionic terpolymer tends to adhere to the outer surface of microcapsules to form a deformable viscous gel layer. When used in a consumer product application, such as treating fabrics or hair in a typical wash/rinse solution and process, the viscous gel layer tends to increase contact area between the polyacrylate microcapsules and the treated surfaces resulting in increased resistance force against rinse water flow. These hydrophobic gels tend to more effectively deposit and adhere to the treated surfaces, such as the treated fibers of a fabric or the treated hair of a consumer, thereby increasing the deposition of the nonionic terpolymer-coated microcapsules versus microcapsules that are not coated with nonionic terpolymer.

The nonionic terpolymer is combined with the microcapsules, thereby becoming disposed on the outer surface of the microcapsules, before the microcapsules are combined with the consumer product adjunct ingredients to form the consumer product compositions of the present invention.

Nonionic terpolymer is preferably incorporated in the present invention in an amount of from about 0.01% to about 8%, preferably from about 0.05% to about 5%, preferably from about 0.1% to about 3%, preferably from about 0.5% to about 1.5%, by weight of the microcapsules.

The nonionic terpolymer of the present invention preferably has a Water Uptake Value, as measured by the WATER UPTAKE VALUE TEST METHOD herein, of at least about 2 grams/gram, preferably from about 3 to about 50 g/g, preferably from about 4 to about 40 g/g, preferably from about 5 to about 38 g/g, or preferably from about 10 to about 35 g/g.

A preferred nonionic terpolymer has the formula above wherein x is an integer selected such that the monomer units constitute about 85% by weight of the nonionic terpolymer, y is an integer selected such that the monomer units constitute about 12% by weight of the nonionic terpolymer, z is an integer selected such that the monomer units constitute about 3% by weight of the nonionic terpolymer, R1 is $CH_3$, R2 is $CH_3$, and R3 is a $C_{18}$ alkyl group. Such a preferred nonionic terpolymer has a viscosity of about 21 poise, as measured by the VISCOSITY TEST METHOD herein, and a Water Uptake Value of about 34, as measured by the WATER UPTAKE VALUE TEST METHOD herein. Such a preferred nonionic terpolymer is poly(N,N-dimethylacrylamide-co-dimethylaminopropyl-methacrylamide-co-N-octadecylacrylamide).

The nonionic terpolymer of the present invention is made according to the following general procedure. The desired monomers (e.g. AAM, DMAA, DMAPA, DMAPMA, AAA, and/or ODAA) are added to a reaction vessel with a solvent (e.g. ethyl acetate). The reaction vessel is sparged with an inert gas (e.g. nitrogen or argon) to remove oxygen from the system and maintain an inert gas atmosphere in the reaction vessel. The contents of the reaction vessel are heated to an elevated temperature (e.g. 30-60° C.) and an initiator is added. Suitable initiators include 2,2'-azobis(2-methylbutyronitrile) (available from DuPont under the trade name V-67) or 2,2'-azobis(2,4-dimethyl-4-methoxyvaleronitrile) (available from Wako under the trade name V-70). The contents of the reaction vessel are maintained at elevated temperature for several hours (e.g. 24-72 hours). The resulting polymer solution is cooled to about room temperature and then precipitated in a solvent (e.g. ethyl acetate and hexane). The precipitate is isolated and dried.

Block Co-Polymer

The block co-polymer utilized as a deposition polymer in the present invention is a block co-polymer comprising monomers selected from the group consisting of acrylamide ("AAM"), dimethyl acrylamide ("DMAA"), n-alkylacrylate ("AA"), and combinations thereof, wherein such block co-polymers have a formula:

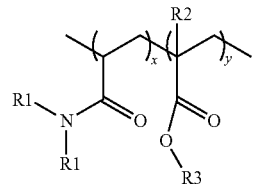

wherein x and y are integers independently selected such that a molar ratio of monomer units represented by x (e.g. AAM or DMAA) to monomer units represented by y (e.g. AA) is from about 1.6:1 to about 2.5:1 by moles of the block co-polymer;

each R1 is independently selected from the group consisting of H and $CH_3$, preferably $CH_3$;

each R2 is independently selected from the group consisting of H and $CH_3$, preferably H; and each R3 is independently a $C_1$-$C_{18}$ alkyl group, preferably a $C_1$-$C_8$ alkyl group, preferably a $C_1$-$C_4$ group, or preferably a $C_3$ alkyl group.

It is believed the effectiveness of the block co-polymer as a coating in improving the deposition of microcapsules onto the surface being treated with the consumer product of the present invention is affected by the number average molecular weight of the polymer (as measured according to the MOLECULAR WEIGHT TEST METHOD herein), and the molar ratio of the monomer units represented by x to the monomer units represented by y. If the number average molecular weight and/or molar ratio is too high, the block co-polymers tends to be insufficiently soluble in water. If the number average molecular weight and/or molar ratio are too low, the block co-polymer tends to insufficiently form a viscoelastic gel on the surface of the coated microcapsules. The effectiveness of the block co-polymer as a coating can also be affected by the Water Uptake Value of the block co-polymer (as measured by the WATER UPTAKE VALUE TEST METHOD herein), which relates to the gelling capacity of the block co-polymer.

The number average molecular weight of the block co-polymer can be determined according to the MOLECULAR WEIGHT TEST METHOD hereinbelow. The block copolymer of the present invention has a number average molecular weight of at least about 11 kDa (kilodaltons), from about 11 to about 45 kDa, preferably from about 15 to about 43 kDa, and preferably from about 20 to about 42 kDa.

Surface charge of the block co-polymer of the present invention is typically nonionic. The block co-polymer is generally coated on the outer surface of the polyacrylate microcapsules due to a favored adhesion energy between two surfaces. The block co-polymer tends to adhere to the outer surface of microcapsules to form a deformable viscous gel layer. These block co-polymers are hydrophobic. These hydrophobic gels tend to more effectively deposit and adhere to the treated surfaces, such as the treated fibers of a fabric or the treated hair of a consumer, thereby increasing the deposition of the block co-polymer-coated microcapsules versus microcapsules that are not coated with block co-polymer.

The block co-polymer is combined with the microcapsules, thereby becoming disposed on the outer surface of the microcapsules, before the microcapsules are combined with the consumer product adjunct ingredients to form the consumer product compositions of the present invention.

Block co-polymer is preferably incorporated in the present invention in an amount of from about 0.01% to about 8%, preferably from about 0.05% to about 5%, preferably from about 0.1% to about 3%, preferably from about 0.5% to about 1.5%, by weight of the microcapsules.

The block co-polymer of the present invention preferably has a Water Uptake Value, as measured by the WATER UPTAKE VALUE TEST METHOD herein, of at least about 2 grams/gram, preferably from about 3 to about 50 g/g, preferably from about 3 to about 25 g/g, preferably from about 3 to about 20 g/g, or preferably from about 3 to about 15 g/g.

A preferred block co-polymer has the formula above wherein x and y are integers selected such that the molar ratio of the monomer units represented by x to the monomer units represented by y is about 1.65 by weight of the block co-polymer, R1 is $CH_3$, R2 is H, and R3 is a $C_3$ alkyl group. Such a preferred block co-polymer has a number average molecular weight of about 42 kDa, as measured by the MOLECULAR WEIGHT TEST METHOD herein, and a Water Uptake Value of about 8, as measured by the WATER UPTAKE VALUE TEST METHOD herein. Such a preferred block co-polymer is poly(N,N-dimethylacrylamide)-poly(n-butylacrylate).

The block co-polymer of the present invention is made according to the following general procedure. The desired n-alkylacrylate monomer is added to a reaction vessel with a solvent (e.g. chlorobenzene), polymerization reagent (e.g. 2-(dodecylthiocarbonothioylthio)-2-methylpropionic acid), and initiator (e.g. 2,2'-azobis(2-methylpropionitrile)). The reaction vessel is sparged with an inert gas (e.g. nitrogen) to remove oxygen from the system and maintain an inert gas atmosphere in the reaction vessel. The contents of the reaction vessel are heated to an elevated temperature (e.g. 65° C.). The contents of the reaction vessel are maintained at elevated temperature for several hours (e.g. 24 hours). The resulting poly(n-alkylacrylate) solution is then precipitated in a solvent (e.g. cold hexane). The precipitate is isolated and dried.

Microcapsules

The consumer product composition of the present invention further comprises a microcapsule, preferably a plurality of microcapsules. The microcapsules comprise a shell material encapsulating a core material which is disposed within the shell material. The shell material comprises a polyacrylate polymer and the core material comprises a benefit agent. The microcapsules have an outer surface on which the deposition polymer is disposed.

Preferred microcapsules comprising a shell material comprising polyacrylate material are described in detail in U.S. Pat. No. 9,186,642, US2011/0269657A1, U.S. Pat. No. 9,221,028, US2011/0268778A1, and U.S. Pat. No. 9,162,085.

The microcapsules of the present invention will typically have a volume weighted median particle size from about 3 microns to about 60 microns. The volume weighted median particle size of the microcapsules can be from about 5 microns to about 45 microns or alternatively from about 8 microns to about 30 microns. The volume weighted median particle size of the microcapsules is determined according to the VOLUME WEIGHTED PARTICLE SIZE TEST METHOD hereinbelow.

Shell Material

The shell material comprises a polyacrylate polymer. The shell material can comprise from about 50% to about 100%, more preferably from about 70% to about 100%, more preferably from about 80% to about 100%, by weight of the shell material, of polyacrylate polymer.

The shell material can optionally further comprise polyvinyl alcohol. The shell material can comprise from about 0.5% to about 40%, preferably from about 0.5% to about 20%, preferably from about 0.5% to about 10%, preferably from about 0.8% to about 5%, by weight of the shell material, of polyvinyl alcohol.

The polyacrylate polymer of the shell material can be derived from a material that comprises one or more multifunctional acrylate moieties. Preferably the multifunctional acrylate moiety is selected from group consisting of tri-functional acrylate, tetra-functional acrylate, penta-functional acrylate, hexa-functional acrylate, hepta-functional acrylate, and mixtures thereof.

The polyacrylate polymer can optionally comprise a moiety selected from the group consisting of an amine acrylate moiety, methacrylate moiety, a carboxylic acid acrylate moiety, carboxylic acid methacrylate moiety, and combinations thereof.

In one aspect, the polyacrylate polymer can be derived from a material that comprises one or more multifunctional acrylate and/or optionally a material that comprises one or more methacrylate moieties, wherein the ratio of material that comprises one or more multifunctional acrylate moieties to material that comprises one or more methacrylate moieties is from about 999:1 to about 6:4, more preferably from about 99:1 to about 8:1, and more preferably from about 99:1 to about 8.5:1. Preferably the multifunctional acrylate moiety is selected from group consisting of tri-functional acrylate, tetra-functional acrylate, penta-functional acrylate, hexa-functional acrylate, hepta-functional acrylate, and mixtures thereof. The polyacrylate polymer can optionally comprise a moiety selected from the group consisting of an amine acrylate moiety, methacrylate moiety, a carboxylic acid acrylate moiety, carboxylic acid methacrylate moiety, and combinations thereof.

The polyacrylate polymer of the shell material preferably comprises a cross-linked polyacrylate polymer.

The polyvinyl alcohol of the shell material, when present, preferably has one or more of the following properties:

a hydrolysis degree from about 55% to about 99%, preferably from about 75% to about 95%, preferably from about 85% to about 90%, preferably from about 87% to about 89%;

a viscosity of from about 40 cps to about 80 cps, preferably from about 45 cps to about 72 cps, preferably from about 45 cps to about 60 cps, preferably 45 cps to 55 cps in 4% water solution at 20° C.;

a degree of polymerization of from about 1500 to about 2500, preferably from about 1600 to about 2200, preferably from about 1600 to about 1900, preferably from about 1600 to about 1800;

a weight average molecular weight of from about 130,000 to about 204,000, preferably from about 146,000 to about 186,000, preferably from about 146,000 to about 160,000, preferably from about 146,000 to about 155,000; and/or a number average molecular weight of from about 65,000 to about 110,000, preferably from about 70,000 to about 101,000, preferably from about 70,000 to about 90,000, preferably from about 70,000 to about 80,000.

Core Material

The core material disposed within the shell material of the microcapsule comprises a benefit agent. The core material can optionally further comprise a partitioning modifier.

Benefit Agents

Benefit agents useful as core material of the microcapsules of the present invention are generally liquid in form at 25° C. The benefit agent is preferably a hydrophobic benefit agent such as perfume. Such hydrophobic benefit agents are typically oils.

Suitable benefit agents can include perfumes, brighteners, dyes, insect repellants, silicones, waxes, flavors, vitamins, fabric softening agents, skin care agents, enzymes, antibacterial agents, bleaches, sensates, and mixtures thereof. Preferably the benefit agent comprises perfume.

The benefit agent of the present invention can comprise perfume. The one or more perfumes may be selected from any perfume or perfume chemical suitable for topical application to the skin and/or hair and suitable for use in personal care compositions, or for providing freshness to fabrics and textiles for use in fabric care compositions. The perfume may be selected from the group consisting of perfumes, highly volatile perfume materials having a boiling point of less than about 250° C., and mixtures thereof. In one aspect, the perfume is selected from high impact accord perfume ingredients having a C log P of greater than about 2 and odor detection thresholds of less than or equal to 50 parts per billion (ppb).

Partitioning Modifier

When the core material of the microcapsule is an oil, such as perfume oil, the properties inherent to the oil may play a role in determining how much, how quickly, and how permeable the resultant shell material of the microcapsule will be when established at the oil/water interface. For example, when the oil of the core material includes highly polar materials, such materials may reduce the diffusion of the monomers and polymers to the oil/water interface, potentially resulting in a relatively thin and highly permeable polymeric shell material, which can lead to an inferior microcapsule. Incorporating a partitioning modifier to adjust the polarity of the core may alter the partitioning coefficient of the polar materials, allowing for the establishment of a thicker, more stable shell material of the microcapsule.

Suitable non-limiting examples of partitioning modifiers are described in detail in US Application Publication No. 2011/0268802. Preferred partitioning modifiers as part of the core material of the present microcapsules are selected from the group consisting of vegetable oil, modified vegetable oil, isopropyl myristate, propan-2-yl tetradecanoate, and mixtures thereof. Suitable vegetable oils are selected from the group consisting of castor oil, soybean oil, and mixtures thereof. Suitable modified vegetable oils are selected from the group consisting of esterified vegetable oil, brominated vegetable oil, and mixtures thereof. Preferred partitioning modifiers are selected from isopropyl myristate, propan-2-yl tetradecanoate, and mixtures thereof.

Process of Making Microcapsules

Suitable processes for making microcapsules comprising a shell material comprising polyacrylate polymer of the present invention are described in detail in U.S. Pat. No. 9,186,642, US2011/0269657A1, U.S. Pat. No. 9,221,028, US2011/0268778A1, and U.S. Pat. No. 9,162,085.

The deposition polymer is added to the polyacrylate microcapsules by mixing the deposition polymer with the microcapsules using a conventional mixing device, such as a spatula, in a conventional mixing container, such as a glass jar. After initial mixing, the mixture is further mixed for several hours in a conventional shaker device at room temperature. On a commercial scale, the deposition polymer can be added to the polyacrylate microcapsules via conventional, commercial-scale mixing equipment.

The resulting deposition polymer-coated microcapsules can be combined with consumer product adjunct ingredients when the microcapsules are in one or more forms, including slurry form, neat particle form, and spray dried particle form. The microcapsules may be combined with the consumer product adjunct ingredients by methods that include mixing and/or spraying.

Consumer Product Adjunct Ingredients

The consumer product compositions of the present invention comprise consumer product adjunct ingredient(s). Suitable non-limiting examples of consumer product adjunct ingredients include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes, structure elasticizing agents, fabric softening agents, hair conditioning agents, carriers, hydrotropes, processing aids, structurants, anti-dandruff agents, anti-agglomeration agents, and/or pigments, and combinations thereof. The precise nature of these additional components, and levels of incorporation thereof, will depend on the physical form of the composition and the nature of the operation for which it is to be used. However, when one or more adjunct materials are present, such one or more adjunct materials may be present as detailed below. The following is a non-limiting list of suitable adjunct materials.

Surfactants—Surfactants utilized may be of the anionic, nonionic, zwitterionic, ampholytic or cationic type or may comprise compatible mixtures of these types. Anionic and nonionic surfactants are typically employed if the composition is a laundry detergent or hair shampoo. In contrast, cationic surfactants are typically employed if the composition is a fabric softener or hair conditioner.

Anionic surfactants suitable for use in the compositions include alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

The compositions may contain a nonionic surfactant. The compositions may contain up to from 0.01% to about 30%, alternatively from about 0.01% to about 20%, more alternatively from about 0.1% to about 10%, by weight of the composition, of a nonionic surfactant. In some examples, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The consumer product compositions may contain up to about 30%, alternatively from about 0.01% to about 20%, more alternatively from about 0.1% to about 20%, by weight of the composition, of a cationic surfactant. Cationic surfactants include those which can deliver fabric care benefits, non-limiting examples which include: fatty amines; quaternary ammonium surfactants; and imidazoline quat materials.

Non-limiting examples of cationic surfactants are N, N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate; 1, 2 di (stearoyl-oxy) 3 trimethyl ammoniumpropane chloride; dialkylenedimethylammonium salts such as dicanoladimethylammonium chloride, di(hard) tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

It will be understood that combinations of cationic surfactants disclosed above are suitable for use herein.

Cationic surfactants can serve as conditioning agents in the consumer product compositions, such as in fabric softening compostions or hair conditioning compositions.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present hair care composition include cocoamphoacetate, cocoamphodiacetate, lauroamphoacetate, lauroamphodiacetate, and mixtures thereof.

Zwitterionic detersive surfactants suitable for use in the hair care composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

Builders—The compositions may also contain from about 0.1% to 80% by weight of the composition of a builder. Compositions in liquid form generally contain from about 1% to 10% by weight of the composition of the builder component. Compositions in granular form generally contain from about 1% to 50% by weight of the composition of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from about 0.5 to about 4.0, or from about 1.0 to about 2.4. Also useful are aluminosilicates including zeolites.

Dispersants—The compositions may contain from about 0.1%, to about 10%, by weight of the composition of dispersants. Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5% by weight of the composition. When enzymes are present, they can be used at very low levels, e.g., from about 0.001% or lower; or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3%, by weight of the composition, of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene-isulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In some examples, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In some examples, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In some examples, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In some examples, the functionalized siloxane polymer may comprise an aminosilicone.

In some examples, the organosilicone may comprise amine ABn silicones and quat ABn silicones. Such organosilicones are generally produced by reacting a diamine with an epoxide.

In some examples, the functionalized siloxane polymer may comprise silicone-urethanes. These are commercially available from Wacker Silicones under the trade name SLM-21200®.

Silicone materials typically serve as conditioning agents in the consumer product compositions, such as in fabric softening compositions or hair conditioning compositions.

Perfume—The consumer product adjunct ingredient can comprise a perfume, which is a neat perfume added to the consumer product composition in addition to the microcapsule. Therefore the consumer product composition can comprise a neat perfume and a microcapsule comprising a perfume as the core material of the microcapsule. The neat perfume and the perfume of the microcapsule can be the same or can be different.

Fabric Hueing Agents—The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes U.S. Pat. No. 8,268,016 B2, or dyes as disclosed in U.S. Pat. No. 7,208,459 B2, and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In some examples, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In some examples, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The hueing agent may be incorporated into the composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

The aforementioned fabric hueing agents can be used in combination (any mixture of fabric hueing agents can be used).

Structurants—Useful structurant materials that may be added to adequately suspend the benefit agent containing delivery particles include polysaccharides, for example, gellan gum, waxy maize or dent corn starch, octenyl succinated starches, derivatized starches such as hydroxyethylated or hydroxypropylated starches, carrageenan, guar gum, pectin, xanthan gum, and mixtures thereof; modified celluloses such as hydrolyzed cellulose acetate, hydroxy propyl cellulose, methyl cellulose, and mixtures thereof; modified proteins such as gelatin; hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Anti-agglomeration agents—Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Conditioning Agents—As discussed previously, the compositions of the present invention, such as fabric conditioning compositions or hair conditioning compositions, can comprise conditioning agents. Suitable conditioning agents are selected from the group consisting of silicone material, cationic surfactant, and mixtures thereof. Such materials are described previously herein.

Aqueous Carrier—The compositions herein can be in the form of pourable liquids (under ambient conditions). Such compositions will therefore typically comprise a carrier, which is present at a level of from about 20 wt % to about 95 wt %, or even from about 60 wt % to about 85 wt %. The carrier may comprise water, or a miscible mixture of water and organic solvent, and in one aspect may comprise water with minimal or no significant concentrations of organic solvent, except as otherwise incidentally incorporated into the composition as minor ingredients of other components.

The carrier useful in embodiments of the composition of the present invention includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Water Uptake Value ("WUV") Test Method

The following test method is used to determine the Water Uptake Value ("WUV") of deposition polymer.

Polymer test materials are analyzed to determine their capacity to take up or absorb water via the water uptake test method herein. This water uptake adsorption capacity is determined by measuring the weight (in grams) of water uptake per gram of dry polymer test material.

Opened-ended, heat-sealable, empty teabag bags are used to contain samples of the test polymer during exposure to water. These empty teabag bags are made from oxygen-bleached filter paper comprising thermoplastic fibers, abaca fibers, and cellulosic fibers, and have bag dimensions of approximately 5.7 cm×6.4 cm (such as those available from the Special Tea Company, Orlando, Fla., U.S.A. Web: www.specialteacompany.com). Ten empty and dry teabag bags are immersed for 24 hours in hard water having a pH of 7, a calcium carbonate hardness of 154 mg/L, and a temperature between 21° C. and 25° C. After the immersion, the empty tea bags are removed from the water and placed on a dry paper towels for 15 seconds to remove excess moisture via blotting. Each of the 10 empty wet bags is weighed individually with an accuracy of ±0.1 mg and the individual weight results are recorded. These weight data values are averaged to determine the average Empty Wet Bag weight.

A mass of between 300 mg and 600 mg of the dry polymer material being tested is weighed into each of ten dry and labelled open-ended teabags. The weight of each of the ten replicate dry polymer test samples is recorded as an Initial Dry Polymer sample weight, and the open edges of the bags are then heat-sealed to secure the polymer sample inside each bag. Each of the ten polymer-filled bags are then immersed for 24 hours in hard water having a pH of 7, a calcium carbonate hardness of 154 mg/L, and a temperature between 21° C. and 25° C. After the immersion, the bags are removed from the water and placed on a dry paper towel for 15 seconds to remove excess moisture via blotting. Each filled, wet bag is then weighed individually with an accuracy of 0.1 mg and the results are recorded as the individual Filled Wet Bag weights.

The average Empty Wet Bag weight is subtracted from each individual Filled Wet Bag weight to calculate the individual Wet Polymer weight for each of the ten samples. For each of the ten samples, the individual weight of Water Taken Up is calculated by subtracting the Initial Dry Polymer sample weight from the Wet Polymer weight, for each sample respectively. Water Uptake per Gram of Dry Polymer is calculated for each of the ten replicate samples, by dividing the individual weight of Water Taken Up by the individual weight of Initial Dry Polymer, for each respective sample, in accordance with the following three equations:

Filled Wet Bag (g)−average Empty Wet Bag (g)=Wet Polymer (g)

Wet Polymer (g)−Initial Dry Polymer (g)=Water Taken Up (g)

Water Taken Up (g)/Initial Dry Polymer (g)=Water Uptake per Gram of Dry Polymer (g/g)

The Water Uptake Values of the sample polymer are calculated from the ten replicate samples and then averaged. This average result is the value that is reported as the Water Uptake Value in grams of water per gram of dry polymer (in units of grams per gram), for the polymer material being tested.

Molecular Weight Test Method—Weight Average

The following test method is used to determine the weight average molecular weight of the deposition polymer, such as chitosan.

Size-exclusion liquid chromatography (LC) is used to determine the Weight-Average Molecular Weight of polymer test material. Chitosan samples (0.1% wt/vol) are dissolved in AcOH/AcNH$_4$ buffer (pH 4.5) and then filtered through a 0.45 um pore size membrane (Millipore). Size-exclusion liquid chromatography (LC) is performed by means of an LC pump (such as the 1260 Infinity pump, Agilent Technologies, Santa Clara, Calif., USA), with two serially-connected columns specifically a model TSK G2500-PW column and a model TSK G6000-PW column, both available from Tosoh Bioscience LLC (King of Prussia, Pa., USA). The detection is achieved via a differential refractometer (such as the model Wyatt Optilab T-rex) coupled on-line with a MALLS detector (such as the model Wyatt Dawn Heleos II) both available from Wyatt Technology Corp. (Santa Barbara, Calif., USA.). Degassed AcOH/AcNH4 buffer (pH 4.5) is used as the eluent after two filtrations through 0.22 um pore size membranes (Millipore). The flow rate is maintained at 0.5 mL/min, and the amount of sample injected is 100 ul. Chromatograms are analyzed by the software such as the Wyatt Astra version 6.1.2 (Wyatt Technology Corp., Santa Barbara, Calif., USA) to calculate the Weight Average Molecular Weight of the polymer test material.

Molecular Weight Test Method—Number Average

The following test method is used to determine the number average molecular weight of the deposition polymer, such as block co-polymer.

The number average molecular weights ("Mn") and weight average molecular weights ("Mw") and polydispersity index ("PDI") of the deposition polymer are determined using gel permeation chromatography ("GPC") with an Agilent 1100 Series HPLC equipped with a PSS SDV Lux column (5 μm) guard column and two PSS SDV Linear XL Lux Columns (5 μm) (linear range of MW=100–3×10$^6$ g/mol), using filtered tetrahydrofuran ("THF") containing 200 ppm 2,6-bis(1,1-dimethylethyl)-4-methylphenol ("BHT") mobile phase at a flow rate of 1.0 mL/min at ambient temperature and miniDAWN TREOS light scattering (60 mW GaAs linearly polarized laser, 658 nm), Optilab rEX differential refractometer (light source=658 nm; Wyatt Technology Corporation) and ViscoStar-II viscometer (Model NO: WV2-03, Wyatt Technology Corporation) detectors.

Samples for analysis are prepared at a known concentration in the range of 1 to 5 mg/mL. The deposition polymer is dissolved in eluent THF and filtered through 0.2 m membrane filters before injection. ASTRA software v. 5.4.14 is used to determine the molecular weight averages and polydispersity. Number average molecular weight and polydispersity index are calculated and reported for the deposition polymer.

Degree of Deacetylation Test Method

The following test method is used to determine the degree of deacetylation of chitosan deposition polymer.

The degree of deacetylation of chitosan test material is determined via Nuclear Magnetic Resonance (NMR) spectroscopy. Chitosan test material (10 mg) is dissolved in 1 mL of dilute acidic D$_2$O (>99.9%, such as available from Aldrich). A Briker NMR instrument model DRX 300 spectrometer (300 MHz) (Bruker Corp., Billerica, Mass., USA) or similar instrument is used to measure the 1H NMR at 298 Kelvin. The 1H chemical shifts are expressed from the signal of 3-(trimethylsilyl) propionic-2,2,3,3-d4 acid sodium salt (>98%, such as available from Aldrich) which is used as an external reference. The degree of deacetylation is calculated from the measured chemical shifts according to standard and widely used approach described in the publication: Hirai et al., Polymer Bulletin 26 (1991), 87-94.

Viscosity Test Method

The following test method is used to determine the viscosity of the deposition polymer.

The viscosity of chitosan test material is determined by measuring a 25° C. 1% (wt/vol) aqueous solution of the chitosan in deionised (DI) water using a model AR1000 rheometer/viscometer from TA instruments (New Castle, Del., USA). The instrument is configured using parallel steel plates of 60 mm diameter, and a gap size of 500 am, and a temperature of 25° C. The reported viscosity is the value measured at 1 s$^{-1}$ and at 25° C., during a logarithmic shear rate sweep from 0.06 s$^{-1}$ to 1000 s$^{-1}$ performed during a 1 minute time period.

Solubility Test Method

The following test method is used to determine the solubility of chitosan deposition polymer in water.

Chitosan solution in various pH buffer are prepared by weighing 25 mg of chitosan polymer in a glass vial followed by the addition of 10 g of pH buffer (pH 2, 4, 7, 10). The chitosan solutions are shortly mixed with a spatula. They are further mixed overnight in a shaker at room temperature. The solubility of Chitosan is assessed visually 24 hours after sample preparation and the solubility is reported as "soluble", "partially soluble", or "insoluble" according to the visual assessment of solubility table below.

Reference pH Buffer Solutions

Available from EMD Millipore Corp. Under the Reference Numbers in the Following Table

| pH | Reference # | pH Buffer Solution Composition | |
|---|---|---|---|
| 2 | 109433 | Citric acid/sodium hydroxide/hydrogen chloride | traceable to SRM from NIST and PTB pH 2.00 (20° C.) Certipur ® |
| 4 | 109435 | Citric acid/sodium hydroxide/hydrogen chloride | traceable to SRM from NIST and PTB pH 4.00 (20° C.) Certipur ® |
| 7 | 109439 | Di-sodium hydrogen phosphate/potassium dihydrogen phosphate | traceable to SRM from NIST and PTB pH 7.00 (20° C.) Certipur ® |

-continued

| pH | Reference # | pH Buffer Solution Composition | |
|---|---|---|---|
| 10 | 109438 | Boric acid/potassium chloride/hydrogen chloride | traceable to SRM from NIST and PTB pH 10.00 (20° C.) Certipur ® |

Visual Assessment of Solubility

| Grading | Definition |
|---|---|
| Soluble | No solid present in solution |
| Partially soluble | There is no solid in solution but there is gelling material (observed by difference of density) |
| Insoluble | Solid present in solution |

Volume Weighted Median Particle Size Test Method

The volume weighted median particle size of the microcapsules of the present invention is determined according to the following test method.

The volume weighted median particle size is measured using an Accusizer 780A, made by Particle Sizing Systems, Santa Barbara Calif. The instrument is calibrated from 0 to 300μ using Duke particle size standards. Samples for particle size evaluation are prepared by diluting about 1 g emulsion, if the volume weighted median particle size of the emulsion is to be determined, or 1 g of capsule slurry, if the finished capsule volume weighted median particle size is to be determined, in about 5 g of de-ionized water and further diluting about 1 g of this solution in about 25 g of water.

About 1 g of the most dilute sample is added to the Accusizer and the testing initiated, using the autodilution feature. The Accusizer should be reading in excess of 9200 counts/second. If the counts are less than 9200 additional sample should be added. The accusizer will dilute the test sample until 9200 counts/second and initiate the evaluation. After 2 minutes of testing the Accusizer will display the results, including volume-weighted median size.

The broadness index can be calculated by determining the particle size at which 95% of the cumulative particle volume is exceeded (95% size), the particle size at which 5% of the cumulative particle volume is exceeded (5% size), and the median volume-weighted median particle size (50% size—50% of the particle volume both above and below this size). Broadness Index (5)=((95% size)−(5% size)/50% size).

Deposition of Microcapsules on Fabric Test Method

The amount of microcapsules deposited onto fabrics in a laundry washing process is evaluated according to the following test method.

1. Product Making
    ARIEL ULTRA heavy duty liquid laundry detergent (available in the United Kingdom) is modified to contain no neat perfume and to which 0.28% of perfume is added via microcapsules comprising the perfume according to the invention.
2. Load Composition
    Perfume ballast load is 3 kg and contains:
        600 g Polyester
        600 g Polycotton
        600 g Muslin (flat) cotton
        600 g Knitted cotton
        600 g Terry towels Ballast loads are preconditioned: 2×70 g Ariel Sensitive, 95° C. wash+2×nil powder, short cotton wash @ 95° C.

After each wash test ballast load is rewashed: 2×70 g Ariel Sensitive, 95° C. wash+2×nil powder, short cotton wash @ 95° C.

For each wash test 6 terry tracers (Maes Textiel) are added.

Tracers are preconditioned: 2×70 g perfume free detergent, 95° C. wash+2×nil powder, short cotton wash @ 95° C. Tracers are not re-used.

3. Wash Conditions
    Before test, washing machine is boil-washed (short cotton wash @ 90° C.).
    Test conditions:
        Miele Softtronic W1714 washing machine is used
        Crease recovery short cycle wash at 30° C., 2 rinses, 1000 rpm spin speed with 67.6 g HDL detergent
        Put load in washing machine, on top place dosing ball with detergent
        Run wash cycle
        Loads are evaluated wet, after 1 day line drying with analytical HeadSpace measurement
    After test, ballast load is re-washed.
    Tracers are not re-used.

Wet and dry fabric samples, originating from rinse/wash cycles, are analyzed by fast headspace GC/MS approach. 4×4 cm part of the terry cotton tracers are transferred to 25 ml headspace vials. The fabric samples are equilibrated for 10 minutes @ 65° C. The headspace above the fabrics is sampled via 23 gauge 50/30UM DVB/CAR/PDMS SPME fiber (Sigma-Aldrich part #57298-U) for 5 minutes. The SPME fiber is subsequently on-line thermally desorbed into the GC. The analyses were analyzed by fast GC/MS in full scan mode. GCMS/SPME: Agilent 6890 GC equipped with 5973 mass spectrometer and Gerstel MPS2 automated SPME sampler, Sigma-Aldrich fiber 57298-U (23 gauge 50/30 um DVB/CAR/PDMS). Vial equilibration: 10 minutes, 65° C., no agitation; Fiber Exposure: 5 minutes, 65° C., no agitation; Desorption 3 minutes, 270° C.; GC Conditions: splitless mode, initial temperature 40° C., 0.5 minutes, 17° C./minute, to 2700 C (0.25 min). GC-Column: Agilent DB-5UI 30 m×0.25×0.25 column (part #122-5532UI). MS-Parameters: from 35 to 300 m/z. The amount of perfume in headspace has been calculated with autoquan macros which calculates the presence of 200 prms and is expressed as nmol/l.

Deposition of Microcapsules on Hair Test Method

The amount of microcapsules deposited onto hair in a hair conditioning process is evaluated according to the following test method.

Pre-Cleaning of Hair Switches: The water of a stationary shower is preset to a temperature of 100 F and a flow rate of 1.5 gallons per minute. 0.1 ml of Sodium Lauryl Ether Sulfate per gram of hair switch is applied to the hair switch that has been pre-wet with tap water and lightly squeegeed. The switch is milked for 30 seconds. Then the switch is rinsed with stationary shower rinse for 30 sec, and then squeegeed. The milking and rinsing process are duplicated. The hair swatches are air dried overnight.

The microcapsule solutions containing 0.1%, by weight, of microcapsules in tap water, or containing 5%, by weight, of microcapsules in PANTENE PRO-V® Hair Conditioner unscented product, are prepared in a 100 g sample jar to form the microcapsule test solutions to be tested.

In a 50 g first sample jar, 4 g of pre-cleaned of hair switch and 20 g of the microcapsule test solution are added. The first sample jar is agitated by hand for 30 sec to saturate the hair switch with the microcapsule test solution. The hair switch is then removed from the first sample jar and placed into a clean, dry 50 g second sample jar and 20 g of rinse water is added to the second sample jar. The solution remaining in the first sample jar is kept for analysis. The second sample jar is agitated by hand for 30 sec to rinse the hair switch with the rinse water. The rinse solution is kept in the second sample jar for analysis. The concentrations of microcapsules in the solutions in the first sample jar and second sample jar are analyzed by Horiba DUAL FL-UV-800-C fluometer. The solutions of the first sample jar and the second sample jar are each transferred to separate testing cuvettes using a plastic transfer pipettes. Each cuvette is placed on the fluometer and running a 3D EEM plus absorbance scan with the following settings: the starting and ending Excitation Wavelengths were 250 nm and 600 nm, respectively; Excitation Wavelength Increment 3 nm; Emission Coverage Increment: 4.66; CCD Gain: Medium; Integration Time: 0.1 second.

Data are analyzed using Aqualog Dual—FL with Origin Software. The process intensity at 318 nm wavelength is selected for data analysis. The amount of microcapsules in each solution are calculated based on calibration curves prepared in the starting tap water solution or 5% conditioner solution. The deposition amount is defined by subtracting the amount of microcapsules in the solution from the first sample jar from the amount of microcapsules in the starting solution. The retention amount is defined by subtracting the amount of microcapsules in the solution from the second sample jar from the deposition amount.

The % Deposition is defined by dividing the deposition amount by the amount of microcapsules in the starting solution. The % Retention is defined by dividing the retention amount by the deposition amount. The % Total Deposition is defined by the % Deposition times the % Retention, divided by 100.

Olfactive Grading on Hair Test Method

The odor performance of a hair conditioner product composition containing polyacrylate microcapsules of the present invention is evaluated according to the following test method.

Analysis steps include:

(a) 0.4 milliliters of PANTENE PRO-V® Hair Conditioner unscented product is applied to a hair switch (IHI, 4 grams, 8 inches long, moderately damaged grade) that has been combed, wet, and lightly squeegeed. Lather switch 50-60 strokes (30 seconds) in a milking action.

(b) Rinse with stationary shower rinse with no manipulation of hair (100 degrees Fahrenheit water temperature, water flow at 1.5 gallons per minute, for 30 seconds, water hardness of 8 grains per gallon). Lightly squeegee once down the hair switch from top to bottom between fingers after rinsing to remove excess water.

(c) Leave hair to dry at ambient temperature by hanging it on a rack. After approximately 3 hours, olfactively grade the hair switch according to the Primavera Grade (0-100 scale for intensity, where a 10 point difference is consumer noticeable). Record this as the Initial Pre-Comb fragrance intensity.

(d) Comb the hair switch 3 times and olfactively grade, record this as the Initial Post-Comb fragrance intensity.

(e) Leave the hair switch under ambient conditions (70 degrees Fahrenheit and 30% relative humidity) for 24 hours. Then, an expert odor panel olfactively grades the hair switch according to the Primavera Grade (0-100 scale for intensity, where a 10 point difference is consumer noticeable), and records this as the 24 hr aged Pre-Comb olfactive intensity.

Comb the hair switches 3 times and assign an olfactive grade, record this as the 24 hr aged Post-Comb olfactive.

Olfactive Grading on Fabric Test Method

The odor performance of a liquid fabric softener product composition containing polyacrylate microcapsules of the present invention is evaluated according to the following test method.

Analysis steps include:

(a) Fabrics are prepared via the following pre-treatment. 2.9±0.1 kg of ballast fabrics containing cotton, polyester, polycotton, and 4 white terry cotton fabric tracers (from Warwick Equest) are washed 4 times with 50 g Non-perfumed Ariel Sensitive (Nordics) at 60° C. with 2 grains per gallon (gpg) water, 1 h 26 min cycle, 1600 rpm, in a front loader washing machine such as Miele (Novotronic W986/Softronic W467/W526/W527/W1614/W1714/W2261) or equivalent and then washed once with no detergent at 60° C. with 2 gpg water. After the last wash, fabrics are dried in a 5 Kg drum tumble drier with hot air outlet such as Miele Novotronic (T490/T220/T454/T430/T410/T7634) or equivalent and then they are ready to be used for testing.

(b) Fabrics are then treated via the following treatment. 2.9±0.1 kg of ballast fabrics containing cotton, polyester, polycotton, and 4 terry cotton fabric tracers (from Warwick Equest) are washed in 15 gpg water at 40° C., 56 minutes cycle, 1200 rpm without laundry detergent to avoid interference in the fabric enhancer evaluation. The fabric softener composition to be tested is pre-diluted in 2 L of 15° C. water with a hardness of 15 gpg 5 min before the starting of the last rinse and added to the last rinse while the washing machine is taking the water. This is a requirement to ensure homogeneous dispensability over the load and minimize the variability of the test results. All fabrics are line dried in a control temperature (25° C.) and humidity (60%) room for 24 hours prior to Olfactive grading.

(c) Wet Fabric samples and dry fabric samples, originating from the above wash and rinse cycles, are graded by the following olfactive grading procedure. All fabrics are line dried in a control temperature (25° C.) and humidity (60%) room for 24 hours prior to Olfactive grading. Wet Fabric Order (WFO) and Dry Fabric Order are graded at the beginning and 24 hours of the drying process according to the Primavera Grade (0-100 scale for intensity, where a 5 point difference is consumer noticeable). Record DFO as the Initial Pre-Rubbing fragrance intensity. Gently rub the fabric 3 times and olfactively grade, record this as the post Rubbing Fabric Odor (RFO) fragrance intensity.

Headspace Test Method

The odor performance of a liquid fabric softening composition containing polyacrylate microcapsules of the present invention is evaluated via a headspace analysis according to the OLFACTIVE GRADING ON FABRIC TEST METHOD above, except that step (c) of the method is replaced with the following headspace analysis step:

(c) Headspace Analysis is performed as follows. The 4 terry cotton fabric tracers treated with fabric softener composition per the method above are used for the analysis. A piece of 5×5 cm is gently cut from the center of each terry cotton fabric tracer and analyzed by fast head space gas chromatography/mass spectroscopy ("GC/MS") using an Agilent DB-5UI 30 m×0.25×0.25 column (part #122-5532UI) in splitless mode. Each white terry cotton fabric is transferred into 25 mL glass headspace vials. The fabric samples are allowed to equilibrate for 10 minutes at 65° C. before the headspace above the fabrics is sampled using a 23 gauge 50/30UM DVB/CAR/PDMS SPME fiber (Sigma-Aldrich part #57298-U) for 5 minutes. The SPME fiber is subsequently on-line thermally desorbed into the GC using a ramp from 40° C. (0.5 min) to 270° C. (0.25 min) at 17° C./min. The perfume raw materials with a molecular weight between 35 and 300 m/z are analyzed by fast GC/MS in full scan mode. The amount of perfume in the headspace is expressed as nmol/L and reported.

Examples

The following are non-limiting synthesis examples of deposition polymers that can be utilized in the present invention.

ethylammonium chloride (herein called "APTAC") and [3-(methyacryloylamino)propyl]trimethylammonium chloride (herein called "MAPTAC"), are all commercially available from Sigma Aldrich. The reaction vessel is sparged with nitrogen to remove oxygen from the system and a nitrogen atmosphere is maintained in the vessel. The reaction vessel and contents are heated to a temperature of 60° C.

Once the contents have reached 60° C., the 10% initiator solution, or 1% initiator solution, from (i) above is added to the reaction vessel in amounts as specified in Table 1 below (1 milliliter or 0.5 milliliter). The reaction is kept at 60° C. for 48 hours.

The following Table 1 set forth non-limiting examples of cationic co-polymers of the present invention (Ex. C1-I1, K1, N1, P1, and Q1), as well as comparative examples of cationic co-polymers that are not of the present invention (Comp. A1, B1, J1, L1, M1, and O1).

TABLE 1

| Polymer | AAM (g) | DMAA (g) | APTAC (g) | MAPTAC (g) | Water (g) | V50 (ml) 1% Solution | V50 (ml) 10% Solution |
|---------|---------|----------|-----------|------------|-----------|-------------|--------------|
| Comp. A1 | 8.31 | | 1.70 | | 99.20 | | 1 |
| Comp. B1 | 6.60 | | 3.40 | | 98.20 | | 1 |
| Ex. C1 | 6.01 | | 4.01 | | 98.10 | | 1 |
| Ex. D1 | 4.01 | | 6.01 | | 98.10 | 1 | |
| Ex. E1 | 6.01 | | 12.20 | | 88.10 | 1 | |
| Ex. F1 | 1.40 | | 8.60 | | 98.10 | 1 | |
| Ex. G1 | 0 | | 30.00 | | 80.10 | 1 | |
| Ex. H1 | 8.31 | | 1.70 | | 99.20 | 1 | |
| Ex. I1 | 8.85 | | 0.98 | | 98.20 | 1 | |
| Comp. J1 | 16.79 | | 5.42 | | 88.10 | 1 | |
| Ex. K1 | | 4.03 | 24.76 | | 76.10 | 0.5 | |
| Comp. L1 | 8.29 | | | 1.70 | 98.60 | | 1 |
| Comp. M1 | 6.60 | | | 3.40 | 97.10 | | 1 |
| Ex. N1 | 6.02 | | | 4.01 | 96.10 | | 1 |
| Comp. O1 | 9.50 | | | 0.50 | 99.60 | | 1 |
| Ex. P1 | | 1.99 | | 5.12 | 20.30 | 0.5 | 0.5 |
| Ex. Q1 | | 7.51 | | 2.50 | 22.88 | 0.5 | |

Cationic Co-Polymer Synthesis

The following are examples of microcapsules coated with cationic co-polymer as a deposition polymer of the present invention, as well as comparative examples of microcapsules coated with cationic co-polymer that is not of the present invention. The cationic co-polymers of Examples C1-I1, K1, N1, P1, and Q1, and Comparative Examples A1, B1, J1, L1, M1, and O1 are prepared according to the following synthesis procedure.

(i) Initiator Solution Preparation 10 ml of water is added to a flask along with 1 gram, or 0.1 gram, of 2,2'-azobis(2-methylpropionamidine) dihydrochloride (available from Wako Chemicals GmbH under the trade name V-50) to form a 10% initiator solution, or a 1% initiator solution, respectively. This 10% initiator solution, or 1% initiator solution, is sparged with argon gas to remove oxygen.

(ii) Polymer Preparation

Into a reaction vessel are added the monomers and water in the appropriate amounts listed for each of the Examples and Comparative Examples in Table 1. The monomers, acrylamide (herein called "AAM"), dimethyl acrylamide (herein called "DMAA"), [3-(acryloylamino)propyl]trim- The viscosity of each cationic co-polymer example and comparative example is measured according to the VISCOSITY TEST METHOD herein. The Water Uptake Value of each cationic co-polymer example and comparative example is measured according to the WATER UPTAKE VALUE TEST METHOD herein. The viscosity and Water Uptake Value of each cationic co-polymer example and comparative example are provided in Table 9 below.

Nonionic Terpolymer Synthesis

The following are examples of microcapsules coated with nonionic terpolymer as a deposition polymer of the present invention, as well as comparative examples of microcapsules coated with nonionic terpolymer that is not of the present invention. The nonionic terpolymers of Examples G2, H2, K2, and L2, and Comparative Examples A2-F2, I2, and J2 are prepared according to the following synthesis procedure.

Examples of nonionic terpolymers according to the present invention, and comparative nonionic terpolymers not of the present invention, are made as follows.

(i) Initiator Solution Preparation 10 ml of ethyl acetate (available from EMD Chemicals) is added to a flask along with 0.2 gram of V-67 (2,2'-azobis (2-methylbutyronitrile) available from DuPont). This 2% solution is sparged with argon gas to remove oxygen.

(ii) Polymer Preparation

Into a reaction vessel are added the monomers and solvent (ethyl acetate or toluene) in the appropriate amounts listed for each of the Examples and Comparative Examples in Table 2a/2b. The monomers include N,N-dimethylacrylamide (DMAA) available from Sigma Aldrich ("Monomer 1" in Table 2a/2b), N,N-dimethylaminopropylmethacrylamide (DMAPMA) available from Sigma Aldrich ("Monomer 2" in Table 2a/2b), N-octadecyl-acrylamide (ODAA) available from Polysciences, Inc., N-2-ethylhexyl acrylamide available from Aurora Fine Chemicals, LLC, and N-dodecyl acrylamide available from TCI (these last 3 monomers representing "Monomer 3" in Table 2a/2b). The solvent, ethyl acetate or toluene, is available from EMD Chemicals or Sigma Aldrich, respectively.

The reaction vessel is closed and heated to the temperature listed in Table 2a/2b (Rxn Temp ° C.). Once at temperature, the reaction vessel is opened and the contents are sparged with an inert gas, such as but not limited to nitrogen or argon, for approximately four minutes utilizing a fritted gas dispersion tube. During the sparge, the initiator solution prepared above containing 2% V-67 is added to the reaction vessel in the amount set forth in Table 2a/2b. The initiator solution is added at approximately ½ sparge time to ensure the initiator solution also undergoes some sparging. The contents are then sealed and kept at the temperature provided in Table 2a/2b for a period of time as indicated in Table 2a/2b (Rxn Time). After the period of time has transpired, the resulting polymer solution is cooled to 23° C.±2.2° C., and then precipitated in ethyl acetate or tolune. The precipitate is isolated from the solvent mixture and dried. Once dried, the resulting polymer product can be used as is, or can be dissolved in solvent system (e.g. water).

The following Table 2a/2b set forth non-limiting examples of nonionic terpolymers of the present invention (Ex. G2, H2, K2, and L2), as well as comparative examples of nonionic terpolymers that are not of the present invention (Comp. A2-F2, I2, and J2).

The viscosity of each nonionic terpolymer example and comparative example is measured according to the VISCOSITY TEST METHOD herein. The Water Uptake Value of each nonionic terpolymer example and comparative example is measured according to the WATER UPTAKE VALUE TEST METHOD herein. The viscosity and Water Uptake Value of each nonionic terpolymer example and comparative example are provided in Table 12 below.

Block Co-Polymer Synthesis

The following are examples of microcapsules coated with block co-polymer as a deposition polymer of the present invention, as well as comparative examples of microcapsules coated with block co-polymer that is not of the present invention. The block co-polymers of Examples C3-G3 and Comparative Examples A3, B3, and H3-N3 are prepared according to the following synthesis procedure.

The block co-polymer of Example C3 of the present invention in Table 3 below is made as follows.

Into a 100 mL round bottom flask is added 5 grams of n-butyl acrylate ("nBA", Molecular Weight 128.17, commercially available from Sigma Aldrich), 0.182 grams of 2-(dodecylthiocarbonothioylthio)-2-methylpropionic acid (commercially available from Sigma Aldrich), 0.0164 grams of 2,2'-azobis(2-methylpropionitrile) (commercially available from Sigma Aldrich) and 40 ml of chlorobenzene (commercially available from Sigma Aldrich). After purging with nitrogen for 20 minutes, the reaction is heated to 65 C for 24 hours. After 24 hours the poly(n-butyl acrylate) is precipitated into cold hexane and dried. The resulting poly (n-butyl acrylate) is characterized by $^1$H NMR in CDCl3 to make sure there is no monomer residual. (Mn=8.41*10$^3$ Daltons, PDI=1.16).

The poly(n-butyl acrylate) is dissolved in 40 mL chlorobenzene with 7 g of N-dimethylacrylamide (DMAA, commercially available from Sigma Aldrich) and 0.0164 grams of 2,2'-azobis (2-methylpropionitrile) (commercially avail- TABLE 2a

| Polymer | Amount Monomer 1 DMAA (g) | Amount Monomer 2 DMAPMA (g) | Monomer 3 | Amount Monomer 3 (g) | Amount Solvent - Ethyl Acetate (g) | Amount (ml) Initiator - V-67 solution | Rxn Temp ° C. | Rxn Time (hours) |
|---|---|---|---|---|---|---|---|---|
| Comp. A2 | 42.55 | 5.05 | C8* | 2.52 | 150 | 1 ml | 50 | 53 |
| Comp. B2 | 42.55 | 3.83 | C8* | 3.83 | 150 | 1 ml | 30 | 70 |
| Comp. C2 | 42.54 | 2.55 | C8* | 5.05 | 150 | 1 ml | 50 | 70 |
| Comp. D2 | 42.56 | 5.11 | C12** | 2/69 | 150 | 1 ml | 50 | 53 |
| Comp. E2 | 42.55 | 3.81 | C12** | 3.77 | 150 | 1 ml | 60 | 24 |
| Comp. F2 | 42.58 | 2.56 | C12** | 5.06 | 150 | 1 ml | 60 | 24 |
| Ex. G2 | 42.56 | 7.08 | C18*** | 0.50 | 150 | 1 ml | 60 | 24 |
| Ex. H2 | 42.55 | 6.28 | C18*** | 1.51 | 150 | 1 ml | 60 | 24 |

*C8 is N-2-ethylhexyl acrylamide
**C12 is N-dodecyl acrylamide
***C18 is Octadecyl Acrylamide TABLE 2b

| Polymer | Monomer 1 DMAA (g) | Monomer 2 DMAPMA (g) | Monomer 3 | Amount Monomer 3 (g) | Amount Solvent - Toluene (g) | Amount (g) Initiator V-67 | Rxn Temp ° C. | Rxn Time (hours) |
|---|---|---|---|---|---|---|---|---|
| Comp. I2 | 42.55 | 6.28 | C18*** | 1.51 | 250 | 0.5 g | 60 | 24 |
| Comp. J2 | 47.53 | 1.02 | C18*** | 1.50 | 250 | 0.5 g | 60 | 24 |
| Ex. K2 | 46.02 | 2.53 | C18*** | 1.50 | 250 | 0.5 g | 60 | 24 |
| Ex. L2 | 38.54 | 10.03 | C18*** | 1.51 | 250 | 0.5 g | 60 | 24 |

***C18 is Octadecyl Acrylamide able from Sigma Aldrich). After purging with nitrogen for 20 minutes, the reaction is heated to 65° C. for 24 hours.

The resulting block co-polymer is precipitated into hexane and dried. The block co-polymer is then characterized by $^1$H NMR and GPC (Mn=2.23*10$^4$ Daltons, PDI=1.182, Molar ratio of DMAA:nBA=1.75:1).

Additional block co-polymers of the present invention (Examples D3-G3) and comparative block co-polymers not of the invention (Comparative Examples A3-B3 and H3-N3) are prepared via the synthesis method as above for Example C3, with the amounts of monomers and reagents adjusted to satisfy the molar ratios specified in Table 3 for each example. The number average molecular weight of each example is measured according to the MOLECULAR WEIGHT TEST METHOD and reported in Tables 3 and 13 below.

TABLE 3

|  | Molar Ratio of Monomers | | |
|---|---|---|---|
| Polymer | Monomer x:N,N-dimethyl acrylamide | Monomer y:n-butylacrylate | Mn (kilodaltons) |
| Comp. A3 | 2.75 | 1 | 40.6 |
| Comp. B3 | 1.89 | 1 | 10.0 |
| Ex. C3 | 1.75 | 1 | 22.3 |
| Ex. D3 | 2.19 | 1 | 39.3 |
| Ex. E3 | 2.02 | 1 | 42.0 |
| Ex. F3 | 2.30 | 1 | 30.8 |
| Ex. G3 | 1.65 | 1 | 42.0 |
| Comp. H3 | 1 | 6 | 79.3 |
| Comp. I3 | 1 | 5 | 67.7 |
| Comp. J3 | 1 | 2 | 72.8 |
| Comp. K3 | 1 | 1 | 46.7 |
| Comp. L3 | 1 | 2 | 118 |
| Comp. M3 | 1.50 | 1 | 21.7 |
| Comp. N3 | 1 | 1 | 18.9 |

The Water Uptake Value of each block co-polymer example and comparative example is measured according to the WATER UPTAKE VALUE TEST METHOD herein, and are provided in Table 13 below.

Additional examples of block co-polymers of the present invention are represented in Table 4 below. Such examples are prepared via the synthesis method as above for Example C3, with the amounts of monomers and reagents adjusted to provide a molar ratio of DMAA to AA of 2:1 for each example. The number average molecular weight of each example is measured according to the MOLECULAR WEIGHT TEST METHOD and reported in Table 4 below.

TABLE 4

| Polymer | Monomer x | Monomer y | Molar Ratio | Mn (kilodaltons) |
|---|---|---|---|---|
| Ex. O3 | N,N-dimethyl acrylamide | Ethyl acrylate | 2:1 | 10.5 |
| Ex. P3 | N,N-dimethyl acrylamide | Propyl acrylate | 2:1 | 12.0 |
| Ex. Q3 | N,N-dimethyl acrylamide | Hexyl acrylate | 2:1 | 13.5 |
| Ex. R3 | N,N-dimethyl acrylamide | Dodecyl acrylate | 2:1 | 11.5 |
| Ex. S3 | N,N-dimethyl acrylamide | Benzyl acrylate | 2:1 | 15.0 |
| Ex. T3 | N,N-dimethyl acrylamide | Phenyl acyrlate | 2:1 | 11.8 |
| Ex. U3 | N,N-dimethyl acrylamide | Ethyl methacrylate | 2:1 | 15.5 |
| Ex. V3 | N,N-dimethyl acrylamide | Hexyl methacrylate | 2:1 | 13.2 |
| Ex. W3 | N,N-dimethyl acrylamide | Dodecyl methacrylate | 2:1 | 11.5 |
| Ex. X3 | N,N-dimethyl acrylamide | Benzyl methacrylate | 2:1 | 10.5 |
| Ex. Y3 | N,N-dimethyl acrylamide | Phenyl methacyrlate | 2:1 | 13.5 |
| Ex. Z3 | N,N-dimethyl acrylamide | Octadecyl acyrlate | 2:1 | 11.7 |

Chitosan Deposition Polymers

The following are examples of microcapsules coated with chitosan deposition polymer having a WUV of at least about 2 g/g of the present invention, as well as comparative examples of microcapsules coated with polymer having WUV of less than about 2 g/g. The chitosan deposition polymers of Examples 1-7 and Comparative Examples A and B are obtained from Laboratorie Ingenierie des Materiaux Polymeres, Universite Claude Bernard Lyon 1, Villeurbanne, France. The chitosan deposition polymers of Examples 8-9 are obtained from Primex ehf, Siglufjordur, Iceland under the trade names PRIMEX 43040 and PRIMEX 40500, respectively. The chitosan deposition polymer of Example 10 is obtained from Sigma Aldrich under Product Number 417963.

The weight average molecular weight, the degree of deacetylation, viscosity, and the Water Uptake Value of each chitosan deposition polymer example are provided in the Table 5 below:

TABLE 5

| Chitosan Example | MW (kDa) | DDA (%) | Viscosity (poise at 1 s$^{-1}$) | Water Uptake Value (g/g) |
|---|---|---|---|---|
| 1 | 574 | 50% | 21.22 | 4.01 |
| 2 | 678 | 75% | 22.71 | 6.83 |
| 3 | 494 | 99% | 21.43 | 5.62 |
| 4 | 76 | 75% | 0.123 | 4.71 |
| 5 | 71 | 99% | 0.158 | 5.58 |
| 6 | 14 | 75% | 0.04 | 5.51 |
| 7 | 11 | 99% | 0.015 | 5.59 |
| 8 | 212 | 79% | 6.88 | 6.83 |
| 9 | 152 | 86% | 0.54 | 5.93 |
| 10 | 198 | 75% | 2.95 | 5.30 |
| Comparative Ex. A | 75 | 52% | 0.065 | 1.75 |
| Comparative Ex. B | 14 | 48% | 0.05 | 1.68 |

Solubility

The chitosans of Examples 1-9 and Comparative Examples A and B are tested according to the SOLUBILITY TEST METHOD above and the results are reported in the chart below. The data indicates whether each chitosan is soluble, partially soluble, or insoluble in water at a given pH.

TABLE 6

| Example | pH 2 | pH 4 | pH 7 | pH 10 |
|---|---|---|---|---|
| 1 | Soluble | Soluble | Soluble | Insoluble |
| 2 | Soluble | Partially soluble | Insoluble | Insoluble |
| 3 | Soluble | Insoluble | Insoluble | Insoluble |
| 4 | Soluble | Partially soluble | Insoluble | Insoluble |
| 5 | Soluble | Insoluble | Insoluble | Insoluble |
| 6 | Soluble | Soluble | Insoluble | Insoluble |
| 7 | Soluble | Insoluble | Insoluble | Insoluble |
| 8 | Soluble | Insoluble | Insoluble | Insoluble |
| 9 | Soluble | Insoluble | Insoluble | Insoluble |

TABLE 6-continued

| Example | pH 2 | pH 4 | pH 7 | pH 10 |
|---|---|---|---|---|
| Comparative Ex. A | Soluble | Soluble | Soluble | Insoluble |
| Comparative Ex. B | Soluble | Soluble | Soluble | Soluble |

Deposition of Microcapsules on Fabric

The chitosan deposition polymers of Examples 1-7 and Comparative Examples A-B are used as coatings for polyacrylate microcapsules as follows. A slurry of polyacrylate microcapsules is obtained from Encapsys (Appleton, Wis., USA) under Reference ID PDS032415 having a volume weighted median particle size of 19.8 microns, 44.7% solids, 21.6% perfume, 45% isopropyl myristate, 1.2% polyvinyl alcohol, pH of 4.34, and the microcapsules having a ratio of core material to shell material of 90:10.

99.75 g of the polyacrylate microcapsule slurry and 0.25 g of the chitosan to be tested is weighed into a glass jar. The ingredients are mixed with a spatula, and are further mixed for several hours in a conventional shaker at room temperature. The resulting chitosan-coated polyacrylate microcapsules comprise about 0.56%, by weight of the microcapsules, of chitosan.

The deposition of the chitosan-coated polyacrylate microcapsules, along with a test sample of uncoated microcapsules as a control, onto fabric are evaluated according to the DEPOSITION OF MICROCAPSULES ON FABRIC TEST METHOD hereinabove. The results of this test are shown in the Table 7 below:

TABLE 7

| Chitosan Example | Mean Total Headspace on Dry Fabric (nmol/L) | Std. Deviation of Total Headspace on Dry Fabric (nmol/L) |
|---|---|---|
| None | 123 | 5 |
| 1 | 178 | 10 |
| 2 | 212 | 14 |
| 3 | 227 | 10 |
| 4 | 185 | 12 |
| 5 | 221 | 7 |
| 6 | 233 | 0 |
| 7 | 246 | 4 |
| Comparative Ex. A | 129 | 5 |
| Comparative Ex. B | 132 | 13 |

Figure 2:
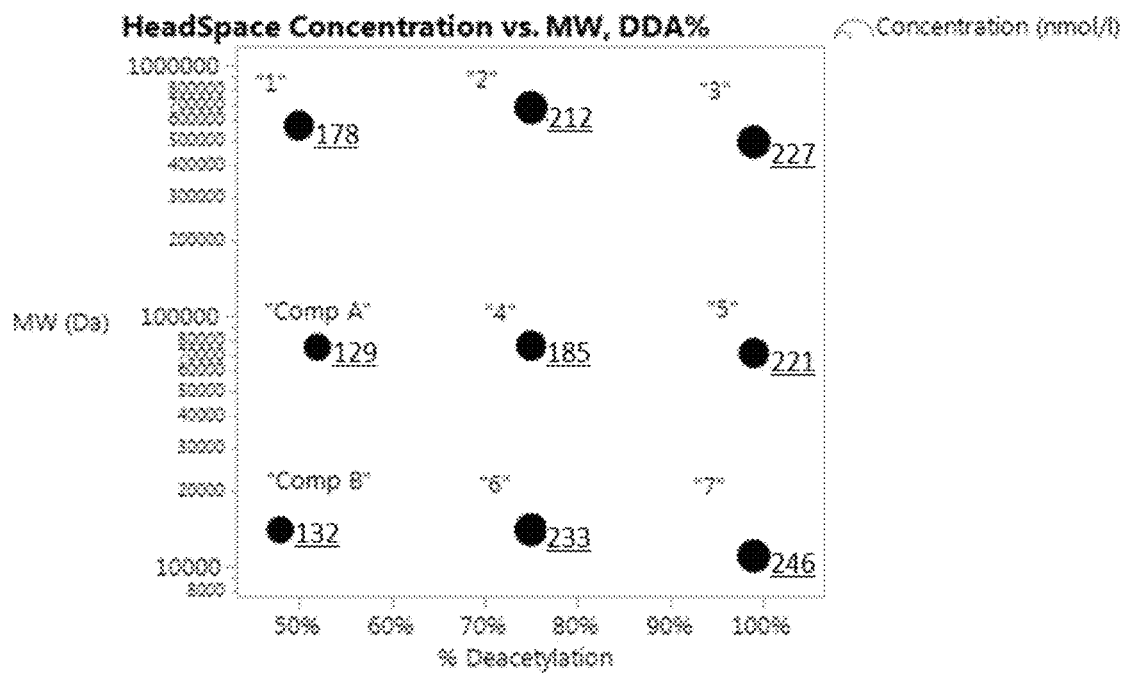
FIG. 2 is plot showing the total headspace concentration over dry terry cotton fabrics of perfume materials released from microcapsules as a function of molecular weight and percent deacetylation of chitosan used to coat the microcapsules.

The data presented in the Table above is plotted in FIG. 2 as Headspace Concentration vs. Weight Average Molecular Weight and Degree of Deacetylation.

Figure 3:
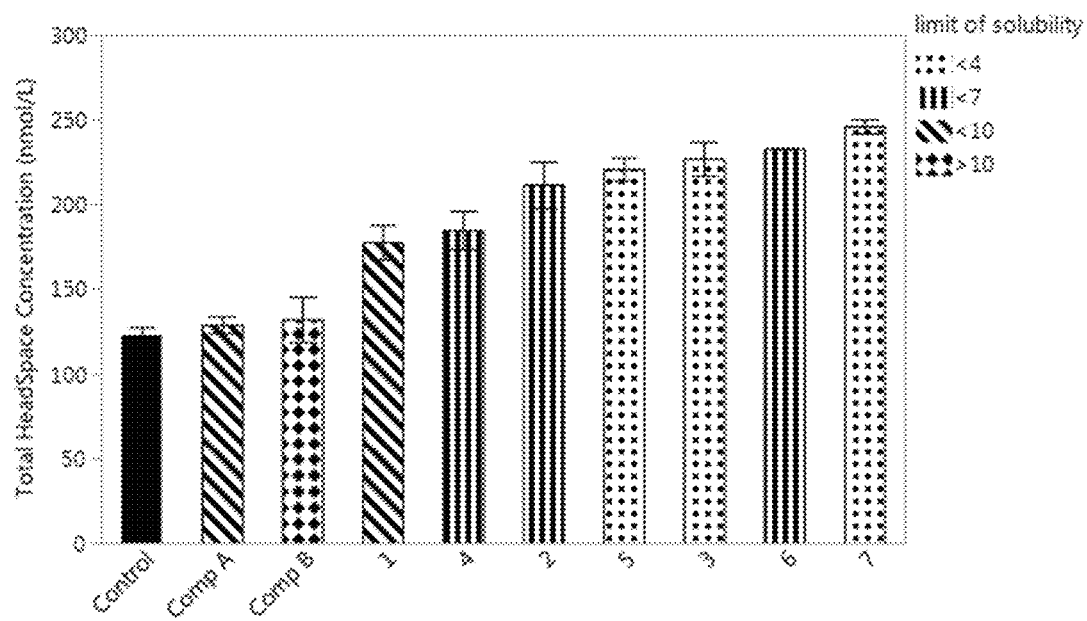
FIG. 3 is a bar chart showing the total headspace concentration over dry terry cotton fabrics of perfume materials released from microcapsules coated with particular chitosan deposition polymers, and microcapsules with no coating of deposition polymer.

The data presented in the Table above is also presented in bar chart format in FIG. 3 as Headspace Concentration for each chitosan example tested, with the solubility of each chitosan example highlighted by the color/shade of the bar for each chitosan example.

As shown by these data, the polyacrylate microcapsules coated with chitosan deposition polymers having a WUV of less than about 2 g/g (i.e. Comparative Examples A and B), as well as the uncoated polyacrylate microcapsules control, provide significantly lower headspace concentration than the polyacrylate microcapsules coated with chitosan deposition polymers having a WUV of at least about 2 g/g of the present invention (i.e. Examples 1-7), which provide higher headspace concentrations, thereby indicating higher amounts of microcapsules being deposited on the treated fabrics.

Deposition of Microcapsules on Hair

The co-polymers are used as coatings for polyacrylate microcapsules as follows. A slurry of polyacrylate microcapsules is obtained from Encapsys (Appleton, Wis., USA) under Reference ID PDS040115B having 44.3% solids and 31.34% perfume oil.

50 g of the polyacrylate microcapsule slurry and 0.222 g of the co-polymer to be tested is weighed into a glass jar. The jar is capped, shaken vigorously by hand, and then mixed for several hours in a conventional shaker at room temperature. The resulting co-polymer-coated polyacrylate microcapsules comprise about 1.0%, by weight of the microcapsules, of co-polymer.

The resulting coated microcapsules are tested for deposition performance on hair according to the DEPOSITION OF MICROCAPSULES ON HAIR METHOD herein, and the results of such testing are reported in Table 8 for chitosan deposition polymers, in Table 9-11 for cationic co-polymer deposition polymers, in Table 12 for nonionic terpolymer deposition polymers, and in Table 13 for block co-polymer deposition polymers, as coatings for polyacrylate microcapsules.

TABLE 8

| Chitosan Example | % Total Deposition on Hair in Tap Water | % Total Deposition on Hair in 5% Conditioner Solution |
|---|---|---|
| None | 31.6 | 3.0 |
| 1 | 35.6 | — |
| 2 | 55.8 | 10 |
| 3 | 39.8 | — |
| 4 | 37.2 | — |
| 5 | 58.4 | — |
| 6 | 52.0 | 12 |
| 7 | 48.8 | — |
| Comparative Ex. A | 31.6 | — |
| Comparative Ex. B | 32.6 | — |

TABLE 9

| Polymer | Ratio of Monomers | Viscosity of 1% Polymer Solution (Poise) | Water Uptake Value (gram of water per gram of polymer) | % Total Deposition on Hair from Tap Water Solution | % Total Deposition on Hair from 5% Conditioner Solution |
|---|---|---|---|---|---|
| None (Uncoated Microcapsules) | | | | 31.6 | 3.0 |
| Comp. A1 | AAM/ APTAC | 83/17 | 0.061 | <0.1 | 31.5 | 3.0 |
| Comp. B1 | | 66/34 | 0.072 | <0.1 | 31.6 | 3.1 |
| Ex. C1 | | 60/40 | 0.091 | 9.8 | 52.0 | 11.2 |
| Ex. D1[1] | | 40/60 | 10.570 | 32.5 | 65.2 | 13.5 |

TABLE 9-continued

| Polymer | Ratio of Monomers | Viscosity of 1% Polymer Solution (Poise) | Water Uptake Value (gram of water per gram of polymer) | % Total Deposition on Hair from Tap Water Solution | % Total Deposition on Hair from 5% Conditioner Solution |
|---|---|---|---|---|---|
| Ex. E1 | | 33/67 | 10.53 | 36.35 | 65.0 | 13.3 |
| Ex. F1 | | 14/86 | 14.2 | 27.53 | 65.5 | 13.5 |
| Ex. G1 | | 0/100 | 2.948 | 38.7 | 63.2 | 12.1 |
| Ex. H1 | | 83/17 | 4.342 | 22.55 | 65.1 | 13.3 |
| Ex. I1 | | 90/10 | 2.657 | 18.71 | 43.5 | 8.3 |
| Comp. J1 | | 95/5 | 4.000 | 18.03 | 29.3 | 2.8 |
| Ex. K1 | DMAA/ APTAC | 14/86 | 5.699 | 17.53 | 65.0 | 13.2 |
| Comp. L1 | AAM/ MAPTAC | 83/17 | 0.072 | <0.1 | 31.5 | 3.0 |
| Comp. M1 | | 66/34 | 0.084 | <0.1 | 31.6 | 3.1 |
| Ex. N1 | | 60/40 | 0.097 | 8.4 | 50.9 | 11.0 |
| Comp. O1 | | 95/5 | 0.801 | 17.6 | 32.0 | 3.1 |
| Ex. P1 | DMAA/ MAPTAC | 28/72 | 7.072 | 39.7 | 52.5 | 11.5 |
| Ex. Q1 | | 75/25 | 4.788 | 30.35 | 51.2 | 11.0 |

[1] The co-polymer of Example D is commercially available from Ashland Specialty Chemical Inc. under the trade name N-Hance SP-100 ™.

The results provided in Table 9 above demonstrate that polyacrylate microcapsules coated with the cationic co-polymer of the present invention exhibit improved deposition versus uncoated polyacrylate microcapsules or polyacrylate microcapsules coated with comparative cationic co-polymer that are not of the present invention.

Polyacrylate microcapsules coated with the cationic co-polymer of Example D1 are prepared as indicated above, which contain 1.00%, 1.40%, 1.75%, and 6.00%, by weight, of the co-polymer of Example D1. The resulting coated microcapsules are tested for deposition performance on hair according to the DEPOSITION OF MICROCAPSULES ON HAIR METHOD herein, and the results of such testing are reported in Table 10 below for each cationic co-polymer coated microcapsules. The thickness of the coating of co-polymer of Example D1 on the surface of the polyacrylate microcapsules is also reported for each sample.

TABLE 10

| Polymer | % Wt. Polymer to in the Slurries | Coating Thickness (nm) | % Total Deposition on Hair in Water | % Total Deposition on Hair in 5% Conditioner Solution |
|---|---|---|---|---|
| None (Uncoated Microcapsules) | 0 | 0 | 31.6 | 3.0 |
| Ex. D1 | 1.00 | 582 | 65.2 | 13.5 |
| Ex. D1 | 1.40 | 800 | 75.0 | 15.0 |
| Ex. D1 | 1.75 | 1000 | 75.5 | 15.2 |
| Ex. D1 | 6.00 | N/A (slurries turn to one piece of gel) | <31.6 | <3.0 |

The results provided in Table 10 above demonstrate that while increasing levels of cationic co-polymer coating the polyacrylate microcapsules can further improve deposition performance on hair, if too much cationic co-polymer is coated on the microcapsules, it can cause the microcapsules in the slurry to agglomerate into a gel.

The cationic co-polymer of Example D1 as a coating for polyacrylate microcapsules is compared with further comparative cationic polymers not of the present invention. Polyacrylate microcapsules coated with the cationic co-polymer of Example D1, and of the comparative cationic polymers, are prepared as indicated above, containing 1.00%, by weight, of the particular polymer. The resulting coated microcapsules are tested for deposition performance on hair according to the DEPOSITION OF MICROCAPSULES ON HAIR METHOD herein, and the results of such testing are reported in Table 11 below for each cationic polymer coated microcapsules. The Water Uptake Values for each cationic polymer are also provided in Table 11 below.

TABLE 11

| Polymer | Water Uptake Value (gram of water per gram of polymer) | % Total Deposition on Hair in Tap Water | % Total Deposition on Hair in 5% Conditioner Solution |
|---|---|---|---|
| None (Uncoated Microcapsules) | NA | 31.6 | 3.0 |
| Ex. D1 | 32.5 | 65.2 | 13.5 |
| Polyquaternium-7 [1] | <0.1 | 30.2 | 2.8 |
| Polyquaternium-76 [2] | <0.1 | 31.5 | 2.9 |
| Polyquaternium-6 [3] | <0.1 | 29.3 | 2.8 |
| Polyquaternium-74 [4] | <0.1 | 26.1 | 2.7 |

[1] Polyquaternium-7 is commercially available from Solvay under the trade name Mirapol 550 ™.
[2] Polyquaternium-76 is commercially available from Solvay under the trade name Mirapol AT-1 ™.
[3] Polyquaternium-6 is commercially available from Solvay under the trade name Mirapol 100 ™.
[4] Polyquaternium-74 is commercially available from Solvay under the trade name Mirapol PQ-74 ™.

The results provided in Table 11 above demonstrate that the structural differences between the cationic co-polymer of the present invention and the comparative cationic polymers, and the resulting difference in Water Uptake Values, can significantly affect the deposition performance of the coated microcapsules on hair.

The uncoated polyacrylate microcapsules above are also tested according to the DEPOSITION OF MICROCAPSULES ON HAIR METHOD herein, wherein the cationic co-polymer of Example D1 is separately added to the 5% conditioner solution containing the uncoated microcapsules at a level of 0.2%, by weight, and at a level of 0.5%, by weight. Such conditioner solutions do not exhibit improved deposition relative to a 5% conditioner solution containing uncoated microcapsules without a cationic co-polymer added. This test demonstrates that separately adding a cationic co-polymer of the present invention to a conditioner composition containing uncoated microcapsules does not provide a deposition benefit, whereas coating polyacrylate microcapsules with a cationic co-polymer of the present invention, and then adding the coated microcapsules to a conditioner composition, does provide an improvement in deposition performance on hair.

TABLE 12

| Polymer | Ratio of Monomers (w/w) DMAA | DMAPMA | AAA (number of C in R3) | Viscosity of 1% Polymer Solution (Poise) | Water Uptake (gram of water per gram of polymer) | % Total Deposition on Hair from Tap Water Solution | % Total Deposition on Hair from 5% Conditioner Solution |
|---|---|---|---|---|---|---|---|
| Comp. A2 | 85 | 10 | 5 (R3 = C$_8$) | 1.68 | 0.1409 | <31.6 | <3.0 |
| Comp. B2 | 85 | 7.5 | 7.5 (R3 = C$_8$) | 1.40 | 0.1042 | <31.6 | <3.0 |
| Comp. C2 | 85 | 5 | 10 (R3 = C$_8$) | 2.37 | 0.1192 | <31.6 | <3.0 |
| Comp. D2 | 85 | 10 | 5 (R3 = C$_{12}$) | 10.90 | 0.7373 | <31.6 | <3.0 |
| Comp. E2 | 85 | 7.5 | 7.5 (R3 = C$_{12}$) | 10.29 | 0.2099 | <31.6 | <3.0 |
| Comp. F2 | 85 | 5 | 10 (R3 = C$_{12}$) | 6.97 | 0.1476 | <31.6 | <3.0 |
| Ex. G2 | 85 | 14 | 1 (R3 = C$_{18}$) | 10.29 | 0.5973 | 41.6 | 18.7 |
| Ex. H2 | 85 | 12 | 3 (R3 = C$_{18}$) | 21.12 | 34.39 | 78.0 | 28.2 |
| Comp. I2 | 95 | 2 | 3 (R3 = C$_{18}$) | 0.68 | 2.74 | <31.6 | <3.0 |
| Comp. J2 | 92 | 5 | 3 (R3 = C$_{18}$) | 0.77 | 2.15 | <31.6 | <3.0 |
| Ex. K2 | 77 | 20 | 3 (R3 = C$_{18}$) | 0.80 | 2.95 | 33.6 | 5.0 |
| Ex. L2 | 67 | 30 | 3 (R3 = C$_{18}$) | 1.30 | 2.97 | 32.5 | 4.5 |
| NONE (Uncoated Microcapsules) | | | | | | 31.6 | <3.0 |

The results provided in Table 12 above demonstrate that polyacrylate microcapsules coated with the nonionic terpolymer of the present invention exhibit improved deposition versus uncoated polyacrylate microcapsules or polyacrylate microcapsules coated with comparative nonionic terpolymer that are not of the present invention.

TABLE 13

| Polymer | Molar Ratio of Monomers Monomer x: DMAA | Monomer y: n-Butylacrylate | Mn (kilodaltons) | Water Uptake Value (gram of water per gram of polymer) | % Total Deposition on Hair in Tap Water | % Total Deposition on Hair in 5% Conditioner Solution |
|---|---|---|---|---|---|---|
| Comp. A3 | 2.75 | 1 | 40.6 | <0.1 | <31.6 | <3.0 |
| Comp. B3 | 1.89 | 1 | 10.0 | <0.1 | <31.6 | <3.0 |
| Ex. C3 | 1.75 | 1 | 22.3 | 12.89 | 75.0 | 25.6 |
| Ex. D3 | 2.19 | 1 | 39.3 | 12.19 | 76.1 | 27.5 |
| Ex. E3 | 2.02 | 1 | 42.0 | 3.49 | 39.5 | 17.8 |
| Ex. F3 | 2.30 | 1 | 30.8 | 3.55 | 41.6 | 18.7 |
| Ex. G3 | 1.65 | 1 | 42.0 | 8.08 | 79.8 | 29.2 |
| Comp. H3 | 1 | 6 | 79.3 | <0.1 | <31.6 | <3.0 |
| Comp. I3 | 1 | 5 | 67.7 | <0.1 | <31.6 | <3.0 |
| Comp. J3 | 1 | 2 | 72.8 | <0.1 | <31.6 | <3.0 |
| Comp. K3 | 1 | 1 | 46.7 | <0.1 | <31.6 | <3.0 |
| Comp. L3 | 1 | 2 | 118 | <0.1 | <31.6 | <3.0 |
| Comp. M3 | 1.50 | 1 | 21.7 | <0.1 | <31.6 | <3.0 |
| Comp. N3 | 1 | 1 | 18.9 | <0.1 | <31.6 | <3.0 |
| NONE (Uncoated Microcapsules) | | | | | 31.6 | <3.0 |

The results provided in Table 13 above demonstrate that polyacrylate microcapsules coated with the block co-polymer of the present invention exhibit improved deposition versus uncoated polyacrylate microcapsules or polyacrylate microcapsules coated with comparative block co-polymer that are not of the present invention.

Olfactive Grading of Deposited Microcapsules on Hair

The deposition polymers of the present invention Examples 8-9 are used as coatings for polyacrylate microcapsules as follows. A slurry of polyacrylate microcapsules is obtained from Encapsys (Appleton, Wis., USA) under Reference ID PDS061814A having a volume weighted median particle size of 6.28 microns, 37.24% solids, 26.35% total oil (perfume and isopropyl myristate), 0.8% polyvinyl alcohol, pH of 4.43, and the microcapsules having a ratio of core material to shell material of 90:10.

50 g of the polyacrylate microcapsule slurry and 0.111 g of the chitosan deposition polymer, or 0.222 g of other deposition polymers, to be tested is weighed into a glass jar. The jar is capped, shaken vigorously by hand, and then mixed for several hours in a conventional shaker at room temperature. The resulting deposition polymer-coated polyacrylate microcapsules comprise about 0.5%, by weight of the microcapsules, of chitosan deposition polymer, or about 1%, by weight of the microcapsules, of other deposition polymers of the present invention.

The long-lasting odor benefits of the resulting deposition polymer-coated microcapsules on hair, versus uncoated microcapsules control, are evaluated by the OLFACTIVE GRADING TEST METHOD hereinabove.

Results of the testing are shown in Table 14 below for chitosan of Examples 8-9, for cationic co-polymer of Example D1, for nonionic terpolymer of Example H2, and for block co-polymer of Example G3.

TABLE 14

| Polymer Example | Olfactive Grading at 24 hour (Pre/Post Comb) |
| --- | --- |
| None | 10/20 |
| 8 | 10/35 |
| 9 | 10/40 |
| Ex. D1 | 10/45 |
| Ex. H2 | 10/50 |
| Ex. G3 | 10/50 |

These data illustrate that the deposition polymer-coated polyacrylate microcapsules of the present invention provide a significant long-lasting odor benefit in-use versus uncoated polyacrylate microcapsules.

Deposition of Microcapsules on Fabric

The deposition polymers are used as coatings for polyacrylate microcapsules as follows. A slurry of polyacrylate microcapsules is obtained from Encapsys (Appleton, Wis., USA) under Reference ID PDS061814A having a volume weighted median particle size of 16.28 microns, 37.24% solids, 26.35% total oil (perfume and isopropyl myristate), 0.8% polyvinyl alcohol, pH of 4.43, and the microcapsules having a ratio of core material to shell material of 90:10.

50 g of the polyacrylate microcapsule slurry and 0.1862 g of the deposition polymer to be tested is weighed into a glass jar. The jar is capped, shaken vigorously by hand, and then mixed for 24 hours in a conventional shaker at room temperature. The resulting deposition polymer-coated polyacrylate microcapsules comprise about 1.0%, by weight of the microcapsules, of deposition polymer.

Test fabric softener compositions are prepared by adding 0.15%, by weight, of coated or uncoated microcapsules, to LENOR® Liquid Fabric Softener unscented.

The long-lasting odor benefits of the resulting polymer-coated microcapsules on fabric, versus uncoated microcapsules, in LENOR® Liquid Fabric Softener, are evaluated by the OLFACTIVE GRADING ON FABRIC TEST METHOD hereinabove. The results of the test are shown in Table 15 below.

TABLE 15

| | Olfactive Grading | | |
| --- | --- | --- | --- |
| Polymer | WFO | DFO | RFO |
| None (Uncoated Microcapsules) | 38 | 43 | 53 |
| Ex. P1 | 50 | 55 | 68 |
| Ex. B1 | 43 | 48 | 55 |
| Ex. D1 | 43 | 48 | 70 |
| Ex. H2 | 43 | 40 | 48 |

The long-lasting odor benefits of the resulting microcapsules coated with block copolymer of the present invention on fabric, versus uncoated microcapsules, in LENOR® Liquid Fabric Softener, are evaluated by the HEADSPACE TEST METHOD hereinabove. Results of the test are shown in Table 16 below:

TABLE 16

| | Headspace (nmol/L) | |
| --- | --- | --- |
| Polymer | Wet Fabric | Dry Fabric |
| None (Uncoated Microcapsules) | 111 | 118 |
| Ex. G | 166 | 152 |

These data illustrate that the polymer-coated polyacrylate microcapsules of the present invention provide a significant long-lasting odor benefit in-use versus uncoated polyacrylate microcapsules when used to treat fabrics.

Polyacrylate Vs. Melamine Formaldehyde Microcapsules

The following illustrates the impact of the deposition polymers of the present invention as a coating on polyacrylate microcapsules as compared to its use as a coating on melamine formaldehyde microcapsules, as well as comparison to uncoated polyacrylate microcapsules and uncoated melamine formaldehyde microcapsules.

A slurry of polyacrylate microcapsules is obtained from Encapsys (Appleton, Wis., USA) under Reference ID PDS032415 having a volume weighted median particle size of 19.8 microns, 44.7% solids, 21.6% perfume, 45% isopropyl myristate, 1.2% polyvinyl alcohol, pH of 4.34, and the microcapsules having a ratio of core material to shell material of 90:10.

99.75 g of the polyacrylate microcapsule slurry and 0.25 g of the chitosan of Example 10, or 0.45 g of the other deposition polymers tested (as indicated in Table 17 below), is weighed into a glass jar. The ingredients are mixed with a spatula, and are further mixed for several hours in a conventional shaker at room temperature. The resulting chitosan-coated polyacrylate microcapsules comprise about 0.56%, by weight of the microcapsules, of chitosan, or about 1%, by weight of the microcapsules, of the other deposition polymers tested.

A slurry of melamine formaldehyde microcapsules is obtained from Encapsys (Appleton, Wis., USA) under Reference ID CH031015-2 having a volume weighted median particle size of 18.7 microns, 36.85% solids, 29.34% perfume, and the microcapsules having a ratio of core material to shell material of 86:14.

99.75 g of the melamine formaldehyde microcapsule slurry and 0.25 g of the chitosan of Example 10 is weighed into a glass jar. The ingredients are mixed with a spatula, and are further mixed for several hours in a conventional shaker at room temperature. The resulting chitosan-coated melamine formaldehyde microcapsules comprise about 0.68%, by weight of the microcapsules, of chitosan, or about 1%, by weight of the microcapsules, of the other deposition polymers tested.

The resulting chitosan-coated microcapsules are tested for deposition performance on terry cotton fabrics and polycotton fabrics according to the DEPOSITION OF MICROCAPSULES ON FABRIC TEST METHOD herein, including comparison to uncoated polyacrylate microcapsules and uncoated melamine formaldehyde microcapsules.

Figure 4:
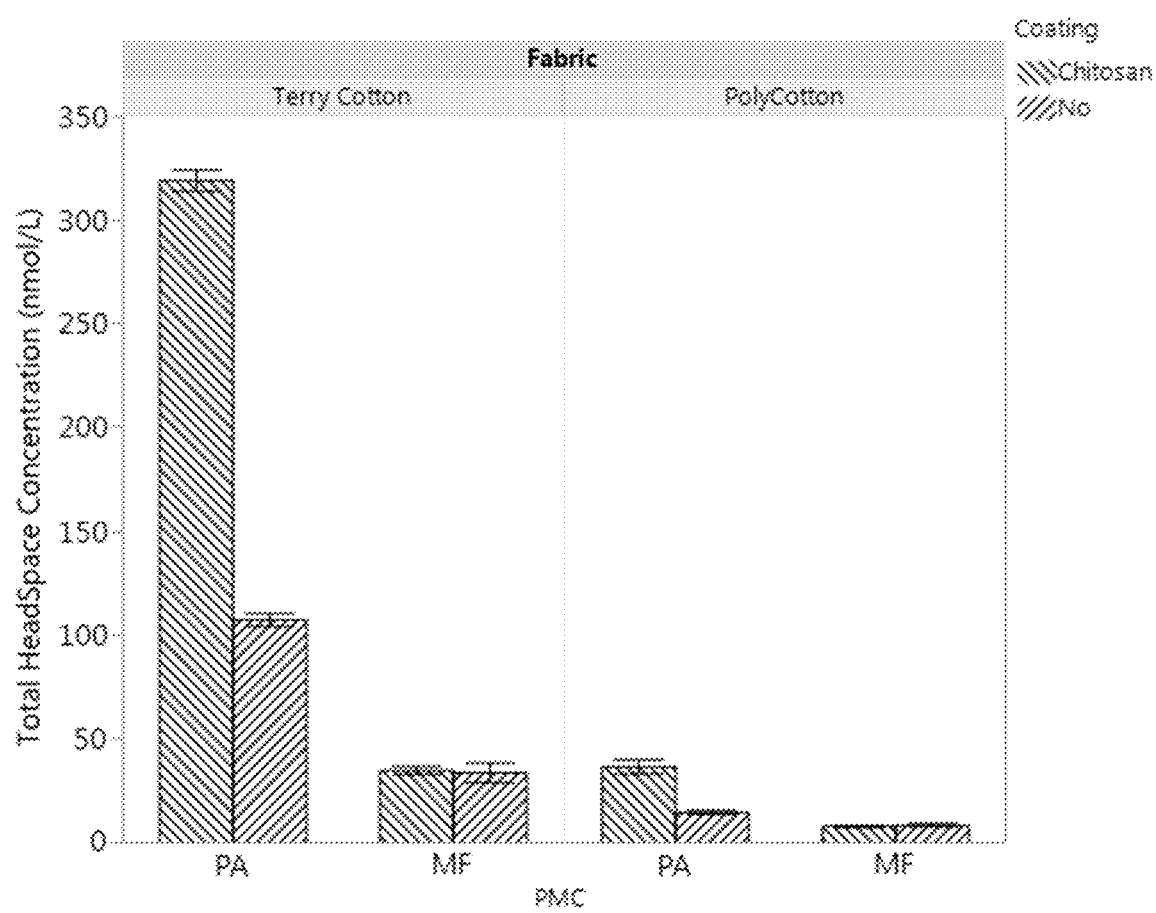
FIG. 4 is a bar chart showing the total headspace concentration over dry terry cotton fabrics of perfume materials released from polyacrylate microcapsules coated with chitosan deposition polymer and from melamine formaldehyde microcapsules coated with chitosan deposition polymer.

The data resulting from this testing is presented in bar chart form in FIG. 4. These data show that coating polyacrylate microcapsules with deposition polymer having a WUV of at least 2 g/g (i.e. 5.30 g/g) of the present invention provides significant deposition benefits whereas coating melamine-formaldehyde microcapsules with the same deposition polymer appears to provide little to no deposition benefits. The benefits associated with coating the microcapsules with the deposition polymer of the present invention therefore appear to be specific to polyacrylate microcapsules.

The resulting coated microcapsules coated with deposition polymers of the present invention, other than chitosan, are tested for deposition performance on hair according to the DEPOSITION OF MICROCAPSULES ON HAIR METHOD herein, including comparison to uncoated polyacrylate microcapsules and uncoated melamine formaldehyde microcapsules. The results are reported in Table 17 below.

TABLE 17

| Type of Microcapsule | Polymer | Olfactive Grading at 24 hour (Pre/Post Comb) |
|---|---|---|
| Polyacrylate Perfume Microcapsules | None (Uncoated Microcapsules) | 10/20 |
| | Ex. D1 | 10/45 |
| | Ex. H2 | 10/50 |
| | Ex. G3 | 10/50 |
| Melamine Formaldehyde Microcapsules | None (Uncoated Microcapsules) | 5/15 |
| | Ex. D1 | 5/15 |
| | Ex. H2 | 5/15 |
| | Ex. G3 | 5/15 |

These data in Table 17 show that coating polyacrylate microcapsules with deposition polymer having a Water Uptake Value of greater than about 2 g/g of the present invention provides significant deposition benefits whereas coating melamine-formaldehyde microcapsules with the same deposition polymers provides little to no deposition benefits. The benefits associated with coating the microcapsules with deposition polymer of the present invention therefore appear to be specific to polyacrylate microcapsules.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising
a consumer product adjunct ingredient;
microcapsules comprising a shell material encapsulating a core material, said core material being disposed within said shell material, wherein said shell material comprises a polyacrylate polymer and said core material comprises a benefit agent; and
deposition polymer having a Water Uptake Value (WUV) of at least about 2 g/g disposed on an outer surface of said microcapsule, wherein said deposition polymer is selected from the group consisting of:
a. chitosan;
b. a cationic co-polymer having a formula:

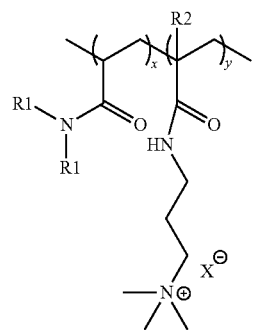

wherein
x is an integer selected such that the monomer units constitute less than 91% by weight of the cationic co-polymer;
y is an integer selected such that the monomer units constitute greater than 9% by weight of the cationic co-polymer;
each R1 is independently selected from the group consisting of H and $CH_3$;
each R2 is independently selected from the group consisting of H and $CH_3$; and
$X^-$ is a charge-balancing anion;

wherein said cationic co-polymer has a viscosity of at least 0.09 poise;

c. a nonionic terpolymer having a formula:

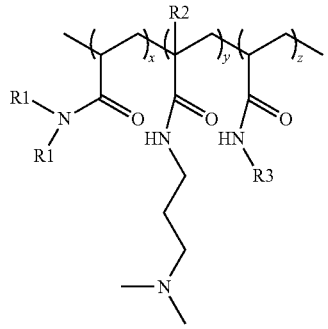

wherein
x is an integer selected such that the monomer units constitute from about 65% to about 91% by weight of the nonionic terpolymer;
y is an integer selected such that the monomer units constitute from about 6% to about 35% by weight of the nonionic terpolymer;
z is an integer selected such that the monomer units constitute from about 1% to about 4% by weight of the nonionic terpolymer;
each R1 is independently selected from the group consisting of H and $CH_3$;
each R2 is independently selected from the group consisting of H and $CH_3$; and
each R3 is independently a $C_{12}$-$C_{32}$ alkyl group;
wherein said nonionic terpolymer has a viscosity of at least 0.8 poise;

d. a block co-polymer having a formula:

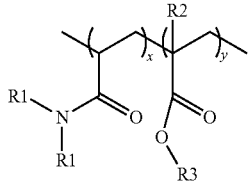

x and y are integers independently selected such that a molar ratio of monomer units represented by x to monomer units represented by y is from about 1.6:1 to about 2.5:1 by weight of the block co-polymer;
each R1 is independently selected from the group consisting of H and $CH_3$;
each R2 is independently selected from the group consisting of H and $CH_3$; and
each R3 is independently a $C_1$-$C_{18}$ alkyl group;
wherein said block co-polymer has a number average molecular weight of at least about 11 kDa; and e. mixtures thereof.

2. The consumer product composition of claim 1, wherein said deposition polymer has a Water Uptake Value of at least about 3 g/g.

3. The consumer product composition of claim 2, wherein said deposition polymer has a Water Uptake Value of at least about 4 g/g.

4. The consumer product composition of claim 1, wherein said deposition polymer is chitosan.

5. The consumer product composition of claim 4, wherein said chitosan has a weight average molecular weight of at least about 100 kDa and/or a degree of deacetylation of at least about 50%.

6. The consumer product composition of claim 4, wherein said chitosan has a degree of de-acetylation of at least about 60% and a weight average molecular weight of at least about 10 kDa.

7. The consumer product composition of claim 4, wherein said chitosan has either:
said weight average molecular weight of at least about 500 kDa and said degree of de-acetylation of at least about 50%, or
said weight average molecular weight of at least about 10 kDa and said degree of de-acetylation of at least about 70%.

8. The consumer product composition of claim 4, wherein said chitosan has a viscosity of at least about 0.01 poise.

9. The consumer product composition of claim 1, wherein said deposition polymer is a cationic co-polymer having a formula:

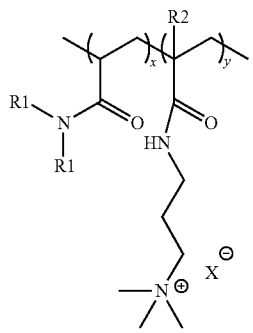

wherein
x is an integer selected such that the monomer units constitute less than 91% by weight of the cationic co-polymer;
y is an integer selected such that the monomer units constitute greater than 9% by weight of the cationic co-polymer;
each R1 is independently selected from the group consisting of H and $CH_3$;
each R2 is independently selected from the group consisting of H and $CH_3$; and
$X^-$ is a charge-balancing anion;
wherein said cationic co-polymer has a viscosity of at least 0.09 poise.

10. The consumer product composition of claim 9, wherein said cationic co-polymer has a viscosity of from 0.09 to about 50 poise.

11. The consumer product composition of claim 9, wherein said cationic co-polymer has a number average molecular weight of from about 10 to about 5,000 kDa.

12. The consumer product composition of claim 9, wherein
x is an integer selected such that the monomer units constitute from about 10% to about 85% by weight of the cationic co-polymer; and
y is an integer selected such that the monomer units constitute from about 15% to about 90% by weight of the cationic co-polymer.

13. The consumer product composition of claim 9, wherein x is an integer selected such that the monomer units constitute about 40% by weight of the cationic co-polymer;

y is an integer selected such that the monomer units constitute about 60% by weight of the cationic co-polymer;

R1 is H; and

R2 is H.

14. The consumer product composition of claim 1, wherein said deposition polymer is a nonionic terpolymer having a formula:

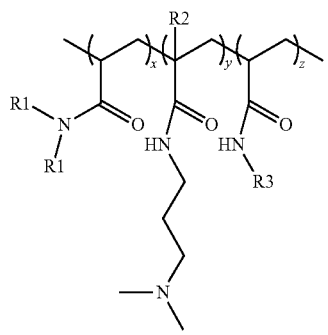

wherein x is an integer selected such that the monomer units constitute from about 65% to about 91% by weight of the nonionic terpolymer;

y is an integer selected such that the monomer units constitute from about 6% to about 35% by weight of the nonionic terpolymer;

z is an integer selected such that the monomer units constitute from about 1% to about 4% by weight of the nonionic terpolymer;

each R1 is independently selected from the group consisting of H and $CH_3$;

each R2 is independently selected from the group consisting of H and $CH_3$; and each R3 is independently a $C_{12}$-$C_{32}$ alkyl group;

wherein said nonionic terpolymer has a viscosity of at least 0.8 poise.

15. The consumer product composition of claim 14, wherein said nonionic terpolymer has a viscosity of from 0.8 to about 50 poise.

16. The consumer product composition of claim 14, wherein said nonionic terpolymer has a number average molecular weight of from about 100 to about 5,000 kDa.

17. The consumer product composition of claim 14, wherein x is an integer selected such that the monomer units constitute from about 67% to about 90% by weight of the nonionic terpolymer;

y is an integer selected such that the monomer units constitute from about 7% to about 30% by weight of the nonionic terpolymer;

z is an integer selected such that the monomer units constitute from about 2% to about 3.5% by weight of the nonionic terpolymer.

18. The consumer product composition of claim 1, wherein said deposition polymer is a block co-polymer having a formula:

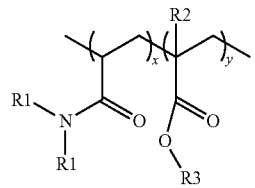

x and y are integers independently selected such that a molar ratio of monomer units represented by x to monomer units represented by y is from about 1.6:1 to about 2.5:1 by weight of the block co-polymer;

each R1 is independently selected from the group consisting of H and $CH_3$;

each R2 is independently selected from the group consisting of H and $CH_3$; and each R3 is independently a $C_1$-$C_{18}$ alkyl group;

wherein said block co-polymer has a number average molecular weight of at least about 11 kDa.

19. The consumer product composition of claim 18, wherein said block co-polymer has a number average molecular weight of from about 11 to about 45 kDa.

20. The consumer product composition of claim 18, wherein x and y are integers independently selected such that the molar ratio of monomer units represented by x to monomer units represented by y is from about 2.5 to about 1 by weight of the block co-polymer.

21. The consumer product composition of claim 1, wherein said deposition polymer is present in an amount of from about 0.01% to about 8%, by weight of the microcapsules.

22. The consumer product composition of claim 1, wherein said benefit agent is a perfume.

23. The consumer product composition of claim 1, wherein said core material further comprises a partitioning modifier selected from the group consisting of vegetable oil, modified vegetable oil, isopropyl myristate, propan-2-yl tetradecanoate, and mixtures thereof.

24. The consumer product composition of claim 1, wherein said polyacrylate polymer comprises a cross-linked polyacrylate polymer.

25. The consumer product composition of claim 1, wherein said polyacrylate polymer comprises a polymer derived from a material comprising a multifunctional acrylate moiety selected from the group consisting of tri-functional acrylate, tetra-functional acrylate, penta-functional acrylate, hexa-functional acrylate, hepta-functional acrylate, and mixtures thereof.

26. The consumer product composition of claim 1, wherein said polyacrylate polymer comprises a moiety selected from the group consisting of amine acrylate moiety, methacrylate moiety, a carboxylic acid acrylate moiety, carboxylic acid methacrylate moiety, and combinations thereof.

27. The consumer product composition of claim 1, wherein said polyacrylate polymer comprises a polymer derived from a first material comprising a multifunctional acrylate moiety.

28. The consumer product composition of claim 1, wherein said shell material further comprises from about 0.5% to about 40%, by weight of said shell material, of polyvinyl alcohol.

29. The consumer product composition of claim 1, wherein said microcapsules have a volume weighted median particle size of from about 3 to about 60 microns.

30. The consumer product composition of claim 1, wherein said deposition polymer is combined with said microcapsules before said microcapsules are combined with said consumer product adjunct ingredient.

31. The consumer product composition of claim 1, wherein said consumer product composition comprises from about 0.001% to about 25%, by weight of the consumer product composition, of said microcapsules.

32. The consumer product composition of claim 1, wherein said consumer product adjunct ingredient is selected from the group consisting of surfactant, conditioning agent, and mixtures thereof.

33. The consumer product composition of claim 32, wherein said surfactant is selected from the group consisting of anionic surfactant, nonionic surfactant, and mixtures thereof.

34. The consumer product composition of claim 32, wherein said conditioning agent is selected from the group consisting of cationic surfactant, a silicone material, and mixtures thereof.

35. The consumer product composition of claim 1, wherein said consumer product composition is encased in a film to form an encased consumer product composition.

36. A method of depositing a microcapsule on a surface, said method comprising the step of contacting said surface with a consumer product composition of claim 1.

37. The method of claim 36, wherein said surface is a fabric.

38. The method of claim 36, wherein said surface is hair.

* * * * *